United States Patent
Nicholas et al.

(10) Patent No.: US 9,663,415 B2
(45) Date of Patent: May 30, 2017

(54) PROCESS FOR MAKING DIESEL BY OLIGOMERIZATION OF GASOLINE

(71) Applicant: UOP LLC, Des Plaines, IL (US)

(72) Inventors: Christopher P. Nicholas, Evanston, IL (US); Steven L. Krupa, Fox River Grove, IL (US); Kurt M. Vanden Bussche, Lake in the Hills, IL (US); Todd M. Kruse, Oak Park, IL (US)

(73) Assignee: UOP LLC, Des Plaines, IL (US)

( * ) Notice: Subject to any disclaimer, the term of this patent is extended or adjusted under 35 U.S.C. 154(b) by 110 days.

(21) Appl. No.: 14/074,703

(22) Filed: Nov. 7, 2013

(65) Prior Publication Data

US 2014/0135554 A1    May 15, 2014

Related U.S. Application Data

(60) Provisional application No. 61/725,335, filed on Nov. 12, 2012.

(51) Int. Cl.
*C07C 2/12* (2006.01)
*C10G 50/00* (2006.01)

(52) U.S. Cl.
CPC ............... *C07C 2/12* (2013.01); *C10G 50/00* (2013.01); *C07C 2529/08* (2013.01); *C07C 2529/40* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 3,516,923 A | 6/1970 | Kirk, Jr. | |
| 3,849,291 A | 11/1974 | Owen | |
| 4,062,801 A | 12/1977 | Burton et al. | |
| 4,304,948 A | 12/1981 | Vora et al. | |
| 4,433,185 A | 2/1984 | Tabak | |
| 4,456,781 A | 6/1984 | Marsh et al. | |
| 4,497,968 A | 2/1985 | Wright et al. | |
| 4,511,747 A | 4/1985 | Wright et al. | |
| 4,513,156 A * | 4/1985 | Tabak | 585/329 |
| 4,544,788 A | 10/1985 | Daviduk et al. | |
| 4,569,827 A * | 2/1986 | Wright et al. | 422/610 |
| 4,822,477 A | 4/1989 | Avidan et al. | |
| 4,837,372 A | 6/1989 | Zimmermann | |
| 4,849,186 A | 7/1989 | Beech et al. | |
| 4,863,585 A | 9/1989 | Herbst et al. | |
| 4,892,643 A | 1/1990 | Herbst et al. | |
| 4,925,996 A | 5/1990 | Mazurek | |
| 4,926,003 A | 5/1990 | Harandi et al. | |
| 4,966,680 A | 10/1990 | Avidan et al. | |
| 5,000,837 A | 3/1991 | Harandi | |
| 5,009,851 A | 4/1991 | Avidan et al. | |
| 5,059,744 A | 10/1991 | Harandi et al. | |
| 5,134,242 A | 7/1992 | Le et al. | |
| 5,324,419 A | 6/1994 | Muldowney | |
| 5,811,608 A | 9/1998 | Stine et al. | |
| 5,849,972 A | 12/1998 | Vicari et al. | |
| 5,895,830 A | 4/1999 | Stine et al. | |
| RE36,403 E | 11/1999 | Krushna | |
| 5,990,367 A | 11/1999 | Stine et al. | |
| 6,049,017 A | 4/2000 | Vora et al. | |
| 6,072,093 A | 6/2000 | O'Neill et al. | |
| 6,111,159 A | 8/2000 | Huff et al. | |
| 6,153,089 A | 11/2000 | Das et al. | |
| 6,222,087 B1 | 4/2001 | Johnson et al. | |
| 6,372,949 B1 | 4/2002 | Brown et al. | |
| 6,399,843 B1 | 6/2002 | Koves | |
| 6,403,853 B1 | 6/2002 | Abrevaya et al. | |
| 6,846,965 B1 | 1/2005 | Schulz et al. | |
| 7,008,527 B2 | 3/2006 | Gauthier et al. | |
| 7,015,174 B2 | 3/2006 | Loezos et al. | |
| 7,183,450 B2 | 2/2007 | Brown et al. | |
| 7,196,238 B2 | 3/2007 | Nurminen et al. | |
| 7,259,285 B1 | 8/2007 | Walter et al. | |
| 7,262,332 B2 | 8/2007 | Duplan et al. | |
| 7,268,268 B2 | 9/2007 | al-Soufi et al. | |
| 7,291,759 B2 | 11/2007 | Heidemann et al. | |
| 7,309,806 B2 | 12/2007 | Loezos et al. | |
| 7,323,099 B2 | 1/2008 | Henry | |
| 7,374,662 B2 | 5/2008 | Duplan et al. | |
| 7,381,853 B2 | 6/2008 | Martens et al. | |
| 7,425,662 B2 | 9/2008 | Stanat et al. | |
| 7,476,773 B2 | 1/2009 | Louret et al. | |
| 7,476,774 B2 | 1/2009 | Umansky et al. | |
| 7,572,947 B2 | 8/2009 | Brown et al. | |

(Continued)

FOREIGN PATENT DOCUMENTS

CN    1915923 A    2/2007
EA    008481 B1    6/2007

(Continued)

OTHER PUBLICATIONS

Bekker, "Butene Oligomerization over Phosphoric Acid: Structural Characterization of Products", Ind. Eng. Chem. Res. 2009, 48, 10156-10162.
Chellappa, "Supercritical alkylation and butene dimerization over sulfated zirconia and iron-manganese promoted sulfated zirconia catalysts", Applied Catalysis A: General 209 (2001) 359-374.
Coetzee, "An improved solid phosphoric acid catalyst for alkene oligomerization in a Fischer-Tropsch refinery", Applied Catalysis A: General 308 (2006) 204-209.
De Klerk, "Oligomerization of Fischer-Tropsch Olefins: Effect of Feed and Operating Conditions on Hydrogenated Motor-Gasoline Quality", Ind. Eng. Chem. Res. 2004, 43, 7449-7455.
Khashagul'Gova, "Heterogeneous catalysts for lower olefin oligomerization", Khimiya Teknologiya Topliv i Masel, n 12, p. 5-6, Dec. 1992.
Kojima, "Butene Okigomerization over Ion-Exchanged Mordenite", Ind. Eng. Chem. Res. 1988, 27, 248-252.

(Continued)

*Primary Examiner* — Jeffrey Mullis

(57) ABSTRACT

Recycle of a stream comprising $C_8$ oligomers to an oligomerization zone to be oligomerized with $C_4$ olefins can produce diesel range oligomers. A diesel stream can be separated from a gasoline stream which can be recycled to the oligomerization zone.

9 Claims, 13 Drawing Sheets

(56) References Cited

U.S. PATENT DOCUMENTS

| | | |
|---|---|---|
| 7,678,953 B2 | 3/2010 | Kuechler et al. |
| 7,705,193 B2 | 4/2010 | Briot et al. |
| 7,737,315 B2 | 6/2010 | Brown et al. |
| 7,803,332 B2 | 9/2010 | Brown et al. |
| 7,834,229 B2 | 11/2010 | Brown et al. |
| 7,847,037 B2 | 12/2010 | Simon |
| 7,847,141 B2 | 12/2010 | Briot et al. |
| 7,919,551 B2 | 4/2011 | De Munck et al. |
| 8,052,945 B2 | 11/2011 | Vora et al. |
| 8,115,042 B2 | 2/2012 | Godsmark et al. |
| 8,128,879 B2 | 3/2012 | da Silva Ferreira Alves et al. |
| 8,137,628 B2 | 3/2012 | Cheiky et al. |
| 8,153,851 B2 | 4/2012 | Gartside et al. |
| 8,178,740 B2 | 5/2012 | Nicholas et al. |
| 8,470,165 B2 | 6/2013 | Cosyns et al. |
| 2003/0116471 A1 | 6/2003 | Zhang et al. |
| 2003/0171632 A1 | 9/2003 | Du Toit |
| 2004/0006250 A1 | 1/2004 | Mathys et al. |
| 2004/0030212 A1 | 2/2004 | Al-Soufi et al. |
| 2005/0121361 A1 | 6/2005 | Duplan et al. |
| 2005/0137435 A1* | 6/2005 | Tiitta et al. ............. 585/329 |
| 2005/0222475 A1 | 10/2005 | Duplan et al. |
| 2005/0288471 A1 | 12/2005 | Bitterlich et al. |
| 2006/0199987 A1 | 9/2006 | Kuechler et al. |
| 2007/0191662 A1 | 8/2007 | Oikarinen et al. |
| 2008/0039669 A1 | 2/2008 | Brown et al. |
| 2008/0287717 A1 | 11/2008 | Kuechler et al. |
| 2009/0193710 A1* | 8/2009 | Xiong et al. ............. 44/449 |
| 2009/0221862 A1 | 9/2009 | Beadle et al. |
| 2009/0240008 A1* | 9/2009 | Simon ............. 526/108 |
| 2009/0292152 A1 | 11/2009 | Brown et al. |
| 2009/0306448 A1 | 12/2009 | Smith, Jr. et al. |
| 2009/0326287 A1 | 12/2009 | Schindler et al. |
| 2010/0036182 A1 | 2/2010 | Forestiere et al. |
| 2010/0113847 A1 | 5/2010 | Kowalik et al. |
| 2010/0158767 A1 | 6/2010 | Mehlberg et al. |
| 2010/0248944 A1 | 9/2010 | Cheng et al. |
| 2010/0286459 A1 | 11/2010 | Gauthier et al. |
| 2010/0331591 A1 | 12/2010 | Brown et al. |
| 2011/0114538 A1 | 5/2011 | Cosyns et al. |
| 2011/0124936 A1 | 5/2011 | Cabiac et al. |
| 2012/0004481 A1 | 1/2012 | Guillon et al. |
| 2012/0029255 A1 | 2/2012 | Digne et al. |
| 2012/0149956 A1 | 6/2012 | Krupa et al. |
| 2012/0283465 A1 | 11/2012 | Hamilton et al. |
| 2013/0079574 A1 | 3/2013 | Luebke et al. |
| 2014/0134058 A1 | 5/2014 | Nicholas et al. |
| 2014/0134059 A1 | 5/2014 | Nicholas et al. |
| 2014/0134064 A1 | 5/2014 | Freet et al. |
| 2014/0135539 A1 | 5/2014 | Nicholas et al. |
| 2014/0135541 A1 | 5/2014 | Nicholas et al. |
| 2014/0135543 A1 | 5/2014 | Nicholas et al. |
| 2014/0135545 A1 | 5/2014 | Wegerer et al. |
| 2014/0135546 A1 | 5/2014 | Nicholas et al. |
| 2014/0135547 A1 | 5/2014 | Nicholas et al. |
| 2014/0135549 A1 | 5/2014 | Freet et al. |
| 2014/0135552 A1 | 5/2014 | Nicholas et al. |
| 2014/0135553 A1 | 5/2014 | Nicholas et al. |
| 2014/0135555 A1 | 5/2014 | Nicholas et al. |
| 2014/0135557 A1 | 5/2014 | Nicholas et al. |

FOREIGN PATENT DOCUMENTS

| | | | |
|---|---|---|---|
| FR | 2673550 | A1 | 9/1992 |
| FR | 2837199 | A1 | 9/2003 |
| FR | 2952646 | A1 | 5/2011 |
| JP | 04220491 | A | 8/1992 |
| JP | 0734076 | A | 2/1995 |
| JP | 2008174682 | A | 7/2008 |
| RU | 2194691 | C2 | 12/2002 |
| WO | 8912036 | A1 | 12/1989 |
| WO | 9925668 | A1 | 5/1999 |
| WO | 2011002631 | A2 | 1/2011 |
| WO | 2012004809 | A1 | 1/2012 |

OTHER PUBLICATIONS

Kuznetsov, "Isobutylene Oligomerization over Zeolitic Catalysts", Neftekhimiya, vol. 21, Issue 6, 849-852 (Nov.-Dec. 1981).

Nocca, "New IFP Technologies for Reformulated Fuels", 1994 Conference on Clean Air Act Implementation and Reformulated Gasolines, Washington, DC, Oct. 9-11, 1994), papers 34P, Oct. 9, 1994.

O'Young, "Skeletal Isomerization of 1-Butene on 10-Member Ring Zeolite Catalysts", Journal of Catalysis 151, 467-469 (1995).

Rakhimov, "The stability of the properties of [various] catalysts for oligomerization of butane-butene fraction", Khimiya i Tekhnologiya Topliv i Masel (ISSN 0023-1169) N.6, 40-41 (1998).

Tabak, "Shape Selective Light Olefin Conversion to Gasoline and Distillate", presented at AIChe Spring National Meeting, Houston, TX, Apr. 2-6, 1989.

Verstraete, "Study of direct and indirect naphtha recycling to a resid FCC unit for maximum propylene production", Catalysis Today 106 (2005) 62-71.

Yang, "Study on reaction kinetics of isobutene oligomerization", J. Univ. Pet. China (Nat. Sci. Ed.), vol. 29, Issue 5, pp. 107-110, Oct. 2005.

Zhou, "Oligomerization of Butene Mixture to Produce High Quality Gasoline", Chinese Journal of Catalysis, vol. 23, No. 6, pp. 487-488, Nov. 2002.

Search Report dated Feb. 20, 2014 for corresponding PCT Appl. No. PCT/US2013/069439.

EP Search Report dated Jun. 17, 2016 for corresponding PCT Application No. PCT/US2013069439.

* cited by examiner

PROCESS FOR MAKING DIESEL BY OLIGOMERIZATION OF GASOLINE

CROSS-REFERENCE TO RELATED APPLICATION

This application claims priority from Provisional Application No. 61/725,335 filed Nov. 12, 2012, the contents of which are hereby incorporated by reference.

BACKGROUND

When oligomerizing light olefins within a refinery, there is frequently a desire to have the flexibility to make high octane gasoline, high cetane diesel, or combination of both. However, catalysts that make high octane gasoline typically make product that is highly branched and within the gasoline boiling point range. This product is very undesirable for diesel. In addition, catalysts that make high cetane diesel typically make product that is more linear and in the distillate boiling point range. This results in less and poorer quality gasoline due to the more linear nature of the product which has a lower octane value.

The oligomerization of butenes is often associated with a desire to make a high yield of high quality gasoline product. There is typically a limit as to what can be achieved when oligomerizing butenes. When oligomerizing butenes, dimerization is desired to obtain gasoline range material. However, trimerization and higher oligomerization can occur which can produce material heavier than gasoline such as diesel. Efforts to produce diesel by oligomerization have failed to provide high yields except through multiple passes.

When oligomerizing olefins from a fluid catalytic cracking (FCC) unit, there is often the desire to maintain a liquid phase within the oligomerization reactors. A liquid phase helps with catalyst stability by acting as a solvent to wash the catalyst of heavier species produced. In addition, the liquid phase provides a higher concentration of olefins to the catalyst surface to achieve a higher catalyst activity. Typically, this liquid phase in the reactor is maintained by hydrogenating some of the heavy olefinic product and recycling this paraffinic product to the reactor inlet.

To maximize propylene produced by the FCC unit, refiners may contemplate oligomerizing FCC olefins to make heavier oligomers and recycling heavier oligomers to the FCC unit. However, some heavy oligomers may be resistant to cracking down to propylene.

The products of olefin oligomerization are usually mixtures of, for example, olefin dimers, trimers, and higher oligomers. Further, each olefin oligomer is itself usually a mixture of isomers, both skeletal and in double bond location. Highly branched isomers are less reactive than linear or lightly branched materials in many of the downstream reactions for which oligomers are used as feedstocks. This is also true of isomers in which access to the double bond is sterically hindered. Olefin types of the oligomers can be denominated according to the degree of substitution of the double bond, as follows:

TABLE 1

| Olefin Type | Structure | Description |
| --- | --- | --- |
| I | R—HC=CH$_2$ | Monosubstituted |
| II | R—HC=CH—R | Disubstituted |
| III | RRC=CH$_2$ | Disubstituted |
| IV | RRC=CHR | Trisubstituted |
| V | RRC=CRR | Tetrasubstituted | wherein R represents an alkyl group, each R being the same or different. Type I compounds are sometimes described as α- or vinyl olefins and Type III as vinylidene olefins. Type IV is sometimes subdivided to provide a Type IVA, in which access to the double bond is less hindered, and Type IVB where it is more hindered.

SUMMARY OF THE INVENTION

We have found that by recycling a stream comprising $C_8$ oligomers to an oligomerization zone to be oligomerized with $C_4$ olefins that diesel range oligomers can be obtained. A diesel stream can be separated from the gasoline stream which can be recycled to the oligomerization zone to oligomerize to make more diesel.

An object of the invention is to provide additional diesel from gasoline.

DEFINITIONS

Figure 1:
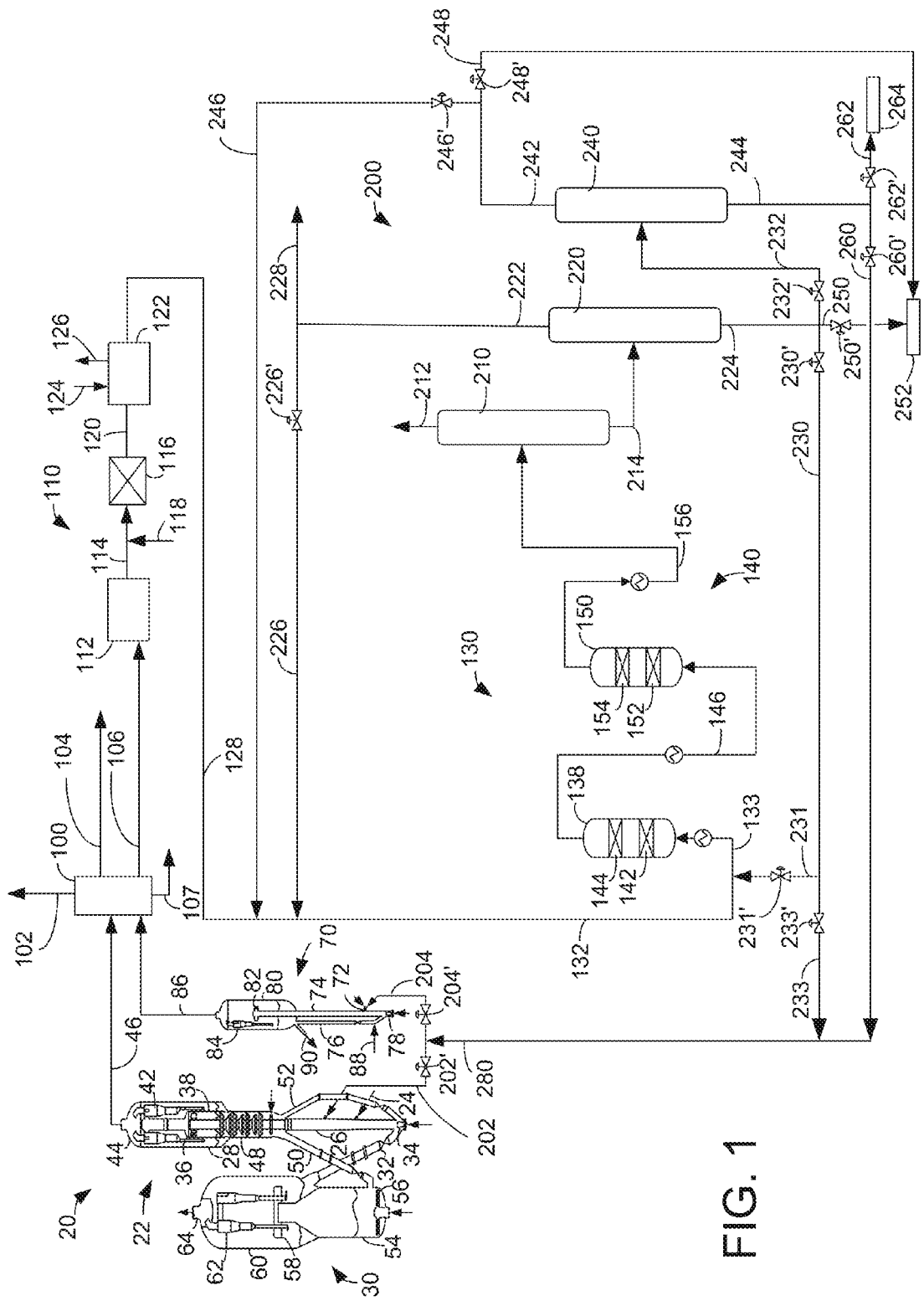
FIG. 1 is a schematic drawing of the present invention.

As used herein, the term "stream" can include various hydrocarbon molecules and other substances. Moreover, the term "stream comprising Cx hydrocarbons" or "stream comprising Cx olefins" can include a stream comprising hydrocarbon or olefin molecules, respectively, with "x" number of carbon atoms, suitably a stream with a majority of hydrocarbons or olefins, respectively, with "x" number of carbon atoms and preferably a stream with at least 75 wt % hydrocarbons or olefin molecules, respectively, with "x" number of carbon atoms. Moreover, the term "stream comprising Cx+ hydrocarbons" or "stream comprising Cx+ olefins" can include a stream comprising a majority of hydrocarbon or olefin molecules, respectively, with more than or equal to "x" carbon atoms and suitably less than 10 wt % and preferably less than 1 wt % hydrocarbon or olefin molecules, respectively, with x−1 carbon atoms. Lastly, the term "Cx− stream" can include a stream comprising a majority of hydrocarbon or olefin molecules, respectively, with less than or equal to "x" carbon atoms and suitably less than 10 wt % and preferably less than 1 wt % hydrocarbon or olefin molecules, respectively, with x+1 carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "substantially" can mean an amount of at least generally about 70%, preferably about 80%, and optimally about 90%, by weight, of a compound or class of compounds in a stream.

As used herein, the term "gasoline" can include hydrocarbons having a boiling point temperature in the range of about 25° to about 200° C. at atmospheric pressure.

As used herein, the term "diesel" or "distillate" can include hydrocarbons having a boiling point temperature in the range of about 150° to about 400° C. and preferably about 200° to about 400° C.

As used herein, the term "vacuum gas oil" (VGO) can include hydrocarbons having a boiling temperature in the range of from 343° to 552° C.

As used herein, the term "vapor" can mean a gas or a dispersion that may include or consist of one or more hydrocarbons.

As used herein, the term "overhead stream" can mean a stream withdrawn at or near a top of a vessel, such as a column.

As used herein, the term "bottom stream" can mean a stream withdrawn at or near a bottom of a vessel, such as a column.

As depicted, process flow lines in the figures can be referred to interchangeably as, e.g., lines, pipes, feeds, gases, products, discharges, parts, portions, or streams.

As used herein, "bypassing" with respect to a vessel or zone means that a stream does not pass through the zone or vessel bypassed although it may pass through a vessel or zone that is not designated as bypassed.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, "taking a stream from" means that some or all of the original stream is taken.

DETAILED DESCRIPTION

The present invention is an apparatus and process that can be used in a first mode to primarily make gasoline, in a second mode to primarily make diesel and in a third mode to make primarily propylene. Gasoline, diesel and propylene are produced in all three modes, but each mode maximizes the primary product intended. The apparatus and process may be described with reference to four components shown in FIG. 1: a fluid catalytic cracking (FCC) zone 20, an FCC recovery zone 100, a purification zone 110, an oligomerization zone 130, and an oligomerization recovery zone 200. Many configurations of the present invention are possible, but specific embodiments are presented herein by way of example. All other possible embodiments for carrying out the present invention are considered within the scope of the present invention.

The fluid catalytic cracking zone 20 may comprise a first FCC reactor 22, a regenerator vessel 30, and an optional second FCC reactor 70.

A conventional FCC feedstock and higher boiling hydrocarbon feedstock are a suitable FCC hydrocarbon feed 24 to the first FCC reactor. The most common of such conventional feedstocks is a VGO. Higher boiling hydrocarbon feedstocks to which this invention may be applied include heavy bottom from crude oil, heavy bitumen crude oil, shale oil, tar sand extract, deasphalted residue, products from coal liquefaction, atmospheric and vacuum reduced crudes and mixtures thereof. The FCC feed 24 may include a recycle stream 280 to be described later.

The first FCC reactor 22 may include a first reactor riser 26 and a first reactor vessel 28. A regenerator catalyst pipe 32 delivers regenerated catalyst from the regenerator vessel 30 to the reactor riser 26. A fluidization medium such as steam from a distributor 34 urges a stream of regenerated catalyst upwardly through the first reactor riser 26. At least one feed distributor injects the first hydrocarbon feed in a first hydrocarbon feed line 24, preferably with an inert atomizing gas such as steam, across the flowing stream of catalyst particles to distribute hydrocarbon feed to the first reactor riser 26. Upon contacting the hydrocarbon feed with catalyst in the first reactor riser 26 the heavier hydrocarbon feed cracks to produce lighter gaseous cracked products while coke is deposited on the catalyst particles to produce spent catalyst.

The resulting mixture of gaseous product hydrocarbons and spent catalyst continues upwardly through the first reactor riser 26 and are received in the first reactor vessel 28 in which the spent catalyst and gaseous product are separated. Disengaging arms discharge the mixture of gas and catalyst from a top of the first reactor riser 26 through outlet ports 36 into a disengaging vessel 38 that effects partial separation of gases from the catalyst. A transport conduit carries the hydrocarbon vapors, stripping media and entrained catalyst to one or more cyclones 42 in the first reactor vessel 28 which separates spent catalyst from the hydrocarbon gaseous product stream. Gas conduits deliver separated hydrocarbon cracked gaseous streams from the cyclones 42 to a collection plenum 44 for passage of a cracked product stream to a first cracked product line 46 via an outlet nozzle and eventually into the FCC recovery zone 100 for product recovery.

Diplegs discharge catalyst from the cyclones 42 into a lower bed in the first reactor vessel 28. The catalyst with adsorbed or entrained hydrocarbons may eventually pass from the lower bed into a stripping section 48 across ports defined in a wall of the disengaging vessel 38. Catalyst separated in the disengaging vessel 38 may pass directly into the stripping section 48 via a bed. A fluidizing distributor delivers inert fluidizing gas, typically steam, to the stripping section 48. The stripping section 48 contains baffles or other equipment to promote contacting between a stripping gas and the catalyst. The stripped spent catalyst leaves the stripping section 48 of the disengaging vessel 38 of the first reactor vessel 28 stripped of hydrocarbons. A first portion of the spent catalyst, preferably stripped, leaves the disengaging vessel 38 of the first reactor vessel 28 through a spent catalyst conduit 50 and passes into the regenerator vessel 30. A second portion of the spent catalyst may be recirculated in recycle conduit 52 from the disengaging vessel 38 back to a base of the first riser 26 at a rate regulated by a slide valve to recontact the feed without undergoing regeneration.

The first riser 26 can operate at any suitable temperature, and typically operates at a temperature of about 150° to about 580° C. at the riser outlet 36. The pressure of the first riser is from about 69 to about 517 kPa (gauge) (10 to 75 psig) but typically less than about 275 kPa (gauge) (40 psig). The catalyst-to-oil ratio, based on the weight of catalyst and feed hydrocarbons entering the riser, may range up to 30:1 but is typically between about 4:1 and about 10:1. Steam may be passed into the first reactor riser 26 and first reactor vessel 28 at a rate between about 2 and about 7 wt % for maximum gasoline production and about 10 to about 15 wt % for maximum light olefin production. The average residence time of catalyst in the riser may be less than about 5 seconds.

The catalyst in the first reactor 22 can be a single catalyst or a mixture of different catalysts. Usually, the catalyst includes two catalysts, namely a first FCC catalyst, and a second FCC catalyst. Such a catalyst mixture is disclosed in, e.g., U.S. Pat. No. 7,312,370 B2. Generally, the first FCC catalyst may include any of the well-known catalysts that are used in the art of FCC. Preferably, the first FCC catalyst includes a large pore zeolite, such as a Y-type zeolite, an active alumina material, a binder material, including either silica or alumina, and an inert filler such as kaolin.

Typically, the zeolites appropriate for the first FCC catalyst have a large average pore size, usually with openings of greater than about 0.7 nm in effective diameter defined by greater than about 10, and typically about 12, member rings. Suitable large pore zeolite components may include synthetic zeolites such as X and Y zeolites, mordenite and faujasite. A portion of the first FCC catalyst, such as the zeolite portion, can have any suitable amount of a rare earth metal or rare earth metal oxide.

The second FCC catalyst may include a medium or smaller pore zeolite catalyst, such as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. Preferably, the second component has the medium or smaller pore zeolite dispersed on a matrix including a binder material such as silica or alumina and an inert filler material such as kaolin. These catalysts may have a crystalline zeolite content of about 10 to about 50 wt % or more, and a matrix material content of about 50 to about 90 wt %. Catalysts containing at least about 40 wt % crystalline zeolite material are typical, and those with greater crystalline zeolite content may be used. Generally, medium and smaller pore zeolites are characterized by having an effective pore opening diameter of less than or equal to about 0.7 nm and rings of about 10 or fewer members. Preferably, the second FCC catalyst component is an MFI zeolite having a silicon-to-aluminum ratio greater than about 15. In one exemplary embodiment, the silicon-to-aluminum ratio can be about 15 to about 35.

The total catalyst mixture in the first reactor 22 may contain about 1 to about 25 wt % of the second FCC catalyst, including a medium to small pore crystalline zeolite, with greater than or equal to about 7 wt % of the second FCC catalyst being preferred. When the second FCC catalyst contains about 40 wt % crystalline zeolite with the balance being a binder material, an inert filler, such as kaolin, and optionally an active alumina component, the catalyst mixture may contain about 0.4 to about 10 wt % of the medium to small pore crystalline zeolite with a preferred content of at least about 2.8 wt %. The first FCC catalyst may comprise the balance of the catalyst composition. The high concentration of the medium or smaller pore zeolite as the second FCC catalyst of the catalyst mixture can improve selectivity to light olefins. In one exemplary embodiment, the second FCC catalyst can be a ZSM-5 zeolite and the catalyst mixture can include about 0.4 to about 10 wt % ZSM-5 zeolite excluding any other components, such as binder and/or filler.

The regenerator vessel 30 is in downstream communication with the first reactor vessel 28. In the regenerator vessel 30, coke is combusted from the portion of spent catalyst delivered to the regenerator vessel 30 by contact with an oxygen-containing gas such as air to regenerate the catalyst. The spent catalyst conduit 50 feeds spent catalyst to the regenerator vessel 30. The spent catalyst from the first reactor vessel 28 usually contains carbon in an amount of from 0.2 to 2 wt %, which is present in the form of coke. An oxygen-containing combustion gas, typically air, enters the lower chamber 54 of the regenerator vessel 30 through a conduit and is distributed by a distributor 56. As the combustion gas enters the lower chamber 54, it contacts spent catalyst entering from spent catalyst conduit 50 and lifts the catalyst at a superficial velocity of combustion gas in the lower chamber 54 of perhaps at least 1.1 m/s (3.5 ft/s) under fast fluidized flow conditions. In an embodiment, the lower chamber 54 may have a catalyst density of from 48 to 320 kg/m$^3$ (3 to 20 lb/ft$^3$) and a superficial gas velocity of 1.1 to 2.2 m/s (3.5 to 7 ft/s). The oxygen in the combustion gas contacts the spent catalyst and combusts carbonaceous deposits from the catalyst to at least partially regenerate the catalyst and generate flue gas.

The mixture of catalyst and combustion gas in the lower chamber 54 ascends through a frustoconical transition section to the transport, riser section of the lower chamber 54. The mixture of catalyst particles and flue gas is discharged from an upper portion of the riser section into the upper chamber 60. Substantially completely or partially regenerated catalyst may exit the top of the transport, riser section. Discharge is effected through a disengaging device 58 that separates a majority of the regenerated catalyst from the flue gas. The catalyst and gas exit downwardly from the disengaging device 58. The sudden loss of momentum and downward flow reversal cause a majority of the heavier catalyst to fall to the dense catalyst bed and the lighter flue gas and a minor portion of the catalyst still entrained therein to ascend upwardly in the upper chamber 60. Cyclones 62 further separate catalyst from ascending gas and deposits catalyst through dip legs into a dense catalyst bed. Flue gas exits the cyclones 62 through a gas conduit and collects in a plenum 64 for passage to an outlet nozzle of regenerator vessel 30. Catalyst densities in the dense catalyst bed are typically kept within a range of from about 640 to about 960 kg/m$^3$ (40 to 60 lb/ft$^3$).

The regenerator vessel 30 typically has a temperature of about 594° to about 704° C. (1100° to 1300° F.) in the lower chamber 54 and about 649° to about 760° C. (1200° to 1400° F.) in the upper chamber 60. Regenerated catalyst from dense catalyst bed is transported through regenerated catalyst pipe 32 from the regenerator vessel 30 back to the first reactor riser 26 through the control valve where it again contacts the first feed in line 24 as the FCC process continues. The first cracked product stream in the first cracked product line 46 from the first reactor 22, relatively free of catalyst particles and including the stripping fluid, exit the first reactor vessel 28 through an outlet nozzle. The first cracked products stream in the line 46 may be subjected to additional treatment to remove fine catalyst particles or to further prepare the stream prior to fractionation. The line 46 transfers the first cracked products stream to the FCC recovery zone 100, which is in downstream communication with the FCC zone 20. The FCC recovery zone 100 typically includes a main fractionation column and a gas recovery section. The FCC recovery zone can include many fractionation columns and other separation equipment. The FCC recovery zone 100 can recover a propylene product stream in propylene line 102, a gasoline stream in gasoline line 104, a light olefin stream in light olefin line 106 and an LCO stream in LCO line 107 among others from the cracked product stream in first cracked product line 46. The light olefin stream in light olefin line 106 comprises an oligomerization feed stream having C$_4$ hydrocarbons including C$_4$ olefins and perhaps having C$_5$ hydrocarbons including C$_5$ olefins.

An FCC recycle stream in recycle line 280 delivers an FCC recycle stream to the FCC zone 20. The FCC recycle stream is directed into a first FCC recycle line 202 with the control valve 202' thereon opened. In an aspect, the FCC recycle stream may be directed into an optional second FCC recycle line 204 with the control valve 204' thereon opened. The first FCC recycle line 202 delivers the first FCC recycle stream to the first FCC reactor 22 in an aspect to the riser 26 at an elevation above the first hydrocarbon feed in line 24. The second FCC recycle line 204 delivers the second FCC recycle stream to the second FCC reactor 70. Typically, both control valves 202' and 204' will not be opened at the same time, so the FCC recycle stream goes through only one of the first FCC recycle line 202 and the second FCC recycle line 204. However, feed through both is contemplated.

The second FCC recycle stream may be fed to the second FCC reactor 70 in the second FCC recycle line 204 via feed distributor 72. The second FCC reactor 70 may include a second riser 74. The second FCC recycle stream is contacted with catalyst delivered to the second riser 74 by a catalyst return pipe 76 to produce cracked upgraded products. The catalyst may be fluidized by inert gas such as steam from distributor 78. Generally, the second FCC reactor 70 may operate under conditions to convert the second FCC recycle stream to second cracked products such as ethylene and propylene. A second reactor vessel 80 is in downstream communication with the second riser 74 for receiving second cracked products and catalyst from the second riser. The mixture of gaseous, second cracked product hydrocarbons and catalyst continues upwardly through the second reactor riser 74 and is received in the second reactor vessel 80 in which the catalyst and gaseous, second cracked products are separated. A pair of disengaging arms may tangentially and horizontally discharge the mixture of gas and catalyst from a top of the second reactor riser 74 through one or more outlet ports 82 (only one is shown) into the second reactor vessel 80 that effects partial separation of gases from the catalyst. The catalyst can drop to a dense catalyst bed within the second reactor vessel 80. Cyclones 84 in the second reactor vessel 80 may further separate catalyst from second cracked products. Afterwards, a second cracked product stream can be removed from the second FCC reactor 70 through an outlet in a second cracked product line 86 in downstream communication with the second reactor riser 74. The second cracked product stream in line 86 is fed to the FCC recovery zone 100, preferably separately from the first cracked products to undergo separation and recovery of ethylene and propylene. Separated catalyst may be recycled via a recycle catalyst pipe 76 from the second reactor vessel 80 regulated by a control valve back to the second reactor riser 74 to be contacted with the second FCC recycle stream.

In some embodiments, the second FCC reactor 70 can contain a mixture of the first and second FCC catalysts as described above for the first FCC reactor 22. In one preferred embodiment, the second FCC reactor 70 can contain less than about 20 wt %, preferably less than about 5 wt % of the first FCC catalyst and at least 20 wt % of the second FCC catalyst. In another preferred embodiment, the second FCC reactor 70 can contain only the second FCC catalyst, preferably a ZSM-5 zeolite.

The second FCC reactor 70 is in downstream communication with the regenerator vessel 30 and receives regenerated catalyst therefrom in line 88. In an embodiment, the first FCC reactor 22 and the second FCC reactor 70 both share the same regenerator vessel 30. Line 90 carries spent catalyst from the second reactor vessel 80 to the lower chamber 54 of the regenerator vessel 30. The catalyst regenerator is in downstream communication with the second FCC reactor 70 via line 90.

The same catalyst composition may be used in both reactors 22, 70. However, if a higher proportion of the second FCC catalyst of small to medium pore zeolite is desired in the second FCC reactor 70 than the first FCC catalyst of large pore zeolite, replacement catalyst added to the second FCC reactor 70 may comprise a higher proportion of the second FCC catalyst. Because the second FCC catalyst does not lose activity as quickly as the first FCC catalyst, less of the second catalyst inventory must be forwarded to the catalyst regenerator 30 in line 90 from the second reactor vessel 80, but more catalyst inventory may be recycled to the riser 74 in return conduit 76 without regeneration to maintain a high level of the second FCC catalyst in the second reactor 70.

The second reactor riser 74 can operate in any suitable condition, such as a temperature of about 425° to about 705° C., preferably a temperature of about 550° to about 600° C., and a pressure of about 140 to about 400 kPa, preferably a pressure of about 170 to about 250 kPa. Typically, the residence time of the second reactor riser 74 can be less than about 3 seconds and preferably is than about 1 second. Exemplary risers and operating conditions are disclosed in, e.g., US 2008/0035527 A1 and U.S. Pat. No. 7,261,807 B2.

Before cracked products can be fed to the oligomerization zone 130, the light olefin stream in light olefin line 106 may require purification. Many impurities in the light olefin stream in light olefin line 106 can poison an oligomerization catalyst. Carbon dioxide and ammonia can attack acid sites on the catalyst. Sulfur containing compounds, oxygenates, and nitriles can harm oligomerization catalyst. Acetylenes and diolefins can polymerize and produce gums on the catalyst or equipment. Consequently, the light olefin stream which comprises the oligomerization feed stream in light olefin line 106 may be purified in an optional purification zone 110.

The light olefin stream in light olefin line 106 may be introduced into an optional mercaptan extraction unit 112 to remove mercaptans to lower concentrations. In the mercaptan extraction unit 112, the light olefin feed may be pre-washed in an optional prewash vessel containing aqueous alkali to convert any hydrogen sulfide to sulfide salt which is soluble in the aqueous alkaline stream. The light olefin stream, now depleted of any hydrogen sulfide, is contacted with a more concentrated aqueous alkali stream in an extractor vessel. Mercaptans in the light olefin stream react with the alkali to yield mercaptides. An extracted light olefin stream lean in mercaptans passes overhead from the extraction column and may be mixed with a solvent that removes COS in route to an optional COS solvent settler. COS is removed with the solvent from the bottom of the settler, while the overhead light olefin stream may be fed to an optional water wash vessel to remove remaining alkali and produce a sulfur depleted light olefin stream in line 114. The mercaptide rich alkali from the extractor vessel receives an injection of air and a catalyst such as phthalocyanine as it passes from the extractor vessel to an oxidation vessel for regeneration. Oxidizing the mercaptides to disulfides using a catalyst regenerates the alkaline solution. A disulfide separator receives the disulfide rich alkaline from the oxidation vessel. The disulfide separator vents excess air and decants disulfides from the alkaline solution before the regenerated alkaline is drained, washed with oil to remove remaining disulfides and returned to the extractor vessel. Further removal of disulfides from the regenerated alkaline stream is also contemplated. The disulfides are run through a sand filter and removed from the process. For more information on mercaptan extraction, reference may be made to U.S. Pat. No. 7,326,333 B2.

In order to prevent polymerization and gumming in the oligomerization reactor that can inhibit equipment and catalyst performance, it is desired to minimize diolefins and acetylenes in the light olefin feed in line 114. Diolefin conversion to monoolefin hydrocarbons may be accomplished by selectively hydrogenating the sulfur depleted stream with a conventional selective hydrogenation reactor 116. Hydrogen may be added to the purified light olefin stream in line 118.

The selective hydrogenation catalyst can comprise an alumina support material preferably having a total surface area greater than 150 $m^2/g$, with most of the total pore volume of the catalyst provided by pores with average diameters of greater than 600 angstroms, and containing surface deposits of about 1.0 to 25.0 wt % nickel and about 0.1 to 1.0 wt % sulfur such as disclosed in U.S. Pat. No. 4,695,560. Spheres having a diameter between about 0.4 and 6.4 mm (1/64 and 1/4 inch) can be made by oil dropping a gelled alumina sol. The alumina sol may be formed by digesting aluminum metal with an aqueous solution of approximately 12 wt % hydrogen chloride to produce an aluminum chloride sol. The nickel component may be added to the catalyst during the sphere formation or by immersing calcined alumina spheres in an aqueous solution of a nickel compound followed by drying, calcining, purging and reducing. The nickel containing alumina spheres may then be sulfided. A palladium catalyst may also be used as the selective hydrogenation catalyst.

The selective hydrogenation process is normally performed at relatively mild hydrogenation conditions. These conditions will normally result in the hydrocarbons being present as liquid phase materials. The reactants will normally be maintained under the minimum pressure sufficient to maintain the reactants as liquid phase hydrocarbons which allow the hydrogen to dissolve into the light olefin feed. A broad range of suitable operating pressures therefore extends from about 276 (40 psig) to about 5516 kPa gauge (800 psig). A relatively moderate temperature between about 25° C. (77° F.) and about 350° C. (662° F.) should be employed. The liquid hourly space velocity of the reactants through the selective hydrogenation catalyst should be above 1.0 $hr^{-1}$. Preferably, it is between 5.0 and 35.0 $hr^{-1}$. The ratio of hydrogen to diolefinic hydrocarbons may be maintained between 0.75:1 and 1.8:1. The hydrogenation reactor is preferably a cylindrical fixed bed of catalyst through which the reactants move in a vertical direction.

A purified light olefin stream depleted of sulfur containing compounds, diolefins and acetylenes exits the selective hydrogenation reactor 116 in line 120. The optionally sulfur and diolefin depleted light olefin stream in line 120 may be introduced into an optional nitrile removal unit (NRU) such as a water wash unit 122 to reduce the concentration of oxygenates and nitriles in the light olefin stream in line 120. Water is introduced to the water wash unit in line 124. An oxygenate and nitrile-rich aqueous stream in line 126 leaves the water wash unit 122 and may be further processed. A drier may follow the water wash unit 122. Other NRU's may be used in place of the water wash unit. A NRU can consist of a group of regenerable beds that adsorb the nitriles and other nitrogen components from the diolefin depleted light olefin stream. Examples of NRU's can be found in U.S. Pat. No. 4,831,206, U.S. Pat. No. 5,120,881 and U.S. Pat. No. 5,271,835.

A purified light olefin oligomerization feed stream perhaps depleted of sulfur containing compounds, diolefins and/or oxygenates and nitriles is provided in oligomerization feed stream line 128. The light olefin oligomerization feed stream in line 128 may be obtained from the cracked product stream in lines 46 and/or 86, so it may be in downstream communication with the FCC zone 20. The oligomerization feed stream need not be obtained from a cracked FCC product stream but may come from another source. The selective hydrogenation reactor 116 is in upstream communication with the oligomerization feed stream line 128. The oligomerization feed stream may comprise $C_4$ hydrocarbons such as butenes, i.e., $C_4$ olefins, and butanes. Butenes include normal butenes and isobutene. The oligomerization feed stream in oligomerization feed stream line 128 may comprise $C_5$ hydrocarbons such as pentenes, i.e., $C_5$ olefins, and pentanes. Pentenes include normal pentenes and isopentenes. Typically, the oligomerization feed stream will comprise about 20 to about 80 wt % olefins and suitably about 40 to about 75 wt % olefins. In an aspect, about 55 to about 75 wt % of the olefins may be butenes and about 25 to about 45 wt % of the olefins may be pentenes. As much as 10 wt %, suitably 20 wt %, typically 25 wt % and most typically 30 wt % of the oligomerization feed may be $C_5$ olefins.

The oligomerization feed line 128 feeds the oligomerization feed stream to an oligomerization zone 130 which may be in downstream communication with the FCC recovery zone 100. The oligomerization feed stream in oligomerization feed line 128 may be mixed with recycle streams from line 226 or 246 prior to entering the oligomerization zone 130 to provide an oligomerization feed stream in an oligomerization feed conduit 132. An oligomerization reactor zone 140 is in downstream communication with the oligomerization feed conduit 132.

In an aspect, an oligomerate return stream in oligomerate return line 231 to be described hereinafter may be mixed with the oligomerization feed stream in oligomerization feed conduit 132 in a first mixed oligomerization feed line 133. The oligomerization feed stream in line 133 may comprise about 10 to about 50 wt % olefins and suitably about 25 to about 40 wt % olefins if the oligomerate return stream from oligomerate return line 231 is mixed with the oligomerization feed stream. Accordingly, the oligomerization feed stream may comprise no more than about 38 wt % butene and in another aspect, the oligomerization feed stream may comprise no more than about 23 wt % pentene. The oligomerization feed stream to the oligomerization zone 130 in mixed oligomerization feed conduit 133 may comprise at least about 10 wt % butene, at least about 5 wt % pentene and preferably no more than about 1 wt % hexene. In a further aspect, the oligomerization feed stream may comprise no more than about 0.1 wt % hexene and no more than about 0.1 wt % propylene. At least about 40 wt % of the butene in the oligomerization feed stream may be normal butene. In an aspect, it may be that no more than about 70 wt % of the oligomerization feed stream is normal butene. At least about 40 wt % of the pentene in the oligomerization feed stream may be normal pentene. In an aspect, no more than about 70 wt % of the oligomerization feed stream in the mixed oligomerization feed conduit 133 may be normal pentene.

The oligomerization reactor zone 140 comprises a first oligomerization reactor 138. The first oligomerization reactor may be preceded by an optional guard bed for removing catalyst poisons that is not shown. The first oligomerization reactor 138 contains the oligomerization catalyst. An oligomerization feed stream may be preheated before entering the first oligomerization reactor 138 in an oligomerization reactor zone 140. The first oligomerization reactor 138 may contain a first catalyst bed 142 of oligomerization catalyst. The first oligomerization reactor 138 may be an upflow reactor to provide a uniform feed front through the catalyst bed, but other flow arrangements are contemplated. In an aspect, the first oligomerization reactor 138 may contain an additional bed or beds 144 of oligomerization catalyst. $C_4$ olefins in the oligomerization feed stream oligomerize over the oligomerization catalyst to provide an oligomerate comprising $C_4$ olefin dimers and trimers. $C_5$ olefins that may be present in the oligomerization feed stream oligomerize over the oligomerization catalyst to provide an oligomerate comprising $C_5$ olefin dimers and trimers and co-oligomerize with $C_4$ olefins to make $C_9$ olefins. The oligomerization produces other oligomers with additional carbon numbers.

We have found that adding $C_5$ olefins to the feed to the oligomerization reactor reduces oligomerization to heavier, distillate range material. This is counterintuitive since one may expect heavier $C_5$ olefins to lead to the formation of more distillate range material. However, when $C_5$ olefins dimerize with themselves or co-dimerize with $C_4$ olefins, the $C_9$ olefins and $C_{10}$ olefins produced do not continue to oligomerize as quickly as $C_8$ olefins produced from $C_4$ olefin dimerization. Thus, the amount of net gasoline produced can be increased. In addition, the resulting $C_9$ olefins and $C_{10}$ olefins in the product have a very high octane value.

Oligomerization effluent from the first bed 142 may optionally be quenched with a liquid such as recycled oligomerate before entering the additional bed 144, and/or oligomerization effluent from the additional bed 144 of oligomerization catalyst may also be quenched with a liquid such as recycled oligomerate to avoid excessive temperature rise. The liquid oligomerate may also comprise oligomerized olefins that can react with the $C_4$ olefins and $C_5$ olefins in the feed and other oligomerized olefins if present to make diesel range olefins. Oligomerized product, also known as oligomerate, exits the first oligomerization reactor 138 in line 146.

In an aspect, the oligomerization reactor zone may include one or more additional oligomerization reactors 150. The oligomerization effluent may be heated and fed to the optional additional oligomerization reactor 150. It is contemplated that the first oligomerization reactor 138 and the additional oligomerization reactor 150 may be operated in a swing bed fashion to take one reactor offline for maintenance or catalyst regeneration or replacement while the other reactor stays online 1n an aspect, the additional oligomerization reactor 150 may contain a first bed 152 of oligomerization catalyst. The additional oligomerization reactor 150 may also be an upflow reactor to provide a uniform feed front through the catalyst bed, but other flow arrangements are contemplated. In an aspect, the additional oligomerization reactor 150 may contain an additional bed or beds 154 of oligomerization catalyst. Remaining $C_4$ olefins in the oligomerization feed stream oligomerize over the oligomerization catalyst to provide an oligomerate comprising $C_4$ olefin dimers and trimers. Remaining $C_5$ olefins, if present in the oligomerization feed stream, oligomerize over the oligomerization catalyst to provide an oligomerate comprising $C_5$ olefin dimers and trimers and co-oligomerize with $C_4$ olefins to make $C_9$ olefins. Over 90 wt % of the $C_4$ olefins in the oligomerization feed stream can oligomerize in the oligomerization reactor zone 140. Over 90 wt % of the $C_5$ olefins in the oligomerization feed stream can oligomerize in the oligomerization reactor zone 140. If more than one oligomerization reactor is used, conversion is achieved over all of the oligomerization reactors 138, 150 in the oligomerization reactor zone 140.

Oligomerization effluent from the first bed 152 may be quenched with a liquid such as recycled oligomerate before entering the additional bed 154, and/or oligomerization effluent from the additional bed 154 of oligomerization catalyst may also be quenched with a liquid such as recycled oligomerate to avoid excessive temperature rise. The recycled oligomerate may also comprise oligomerized olefins that can react with the $C_4$ olefins and $C_5$ olefins in the feed and other oligomerized olefins to increase production of diesel range olefins.

An oligomerate conduit 156, in communication with the oligomerization reactor zone 140, withdraws an oligomerate stream from the oligomerization reactor zone 140. The oligomerate conduit 156 may be in downstream communication with the first oligomerization reactor 138 and the additional oligomerization reactor 150.

The oligomerization reactor zone 140 may contain an oligomerization catalyst. The oligomerization catalyst may comprise a zeolitic catalyst. The zeolite may comprise between 5 and 95 wt % of the catalyst. Suitable zeolites include zeolites having a structure from one of the following classes: MFI, MEL, SFV, SVR, ITH, IMF, TUN, FER, EUO, BEA, FAU, BPH, MEI, MSE, MWW, UZM-8, MOR, OFF, MTW, TON, MTT, AFO, ATO, and AEL. These three-letter codes for structure types are assigned and maintained by the International Zeolite Association Structure Commission in the *Atlas of Zeolite Framework Types*, which is at http://www.iza-structure.org/databases/. In a preferred aspect, the oligomerization catalyst may comprise a zeolite with a framework having a ten-ring pore structure. Examples of suitable zeolites having a ten-ring pore structure include those comprising TON, MTT, MFI, MEL, AFO, AEL, EUO and FER. In a further preferred aspect, the oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the oligomerization catalyst comprises an MTT zeolite.

The oligomerization catalyst may be formed by combining the zeolite with a binder, and then forming the catalyst into pellets. The pellets may optionally be treated with a phosphoric reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark Versal. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable oligomerization catalyst is prepared by mixing proportionate volumes of zeolite and alumina to achieve the desired zeolite-to-alumina ratio. In an embodiment, about 5 to about 80, typically about 10 to about 60, suitably about 15 to about 40 and preferably about 20 to about 30 wt % MTT zeolite and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize surface acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 µm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

In an embodiment, the oligomerization catalyst may be a solid phosphoric acid catalyst (SPA). The SPA catalyst refers to a solid catalyst that contains as a principal ingredient an acid of phosphorous such as ortho-, pyro- or tetraphosphoric acid. SPA catalyst is normally formed by mixing the acid of phosphorous with a siliceous solid carrier to form a wet paste. This paste may be calcined and then crushed to yield catalyst particles or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fuller's earth and iron compounds including iron oxide may be added to the carrier to increase its strength and hardness. The combination of the carrier and the additives preferably comprises about 15-30 wt % of the catalyst, with the remainder being the phosphoric acid. The additive may comprise about 3-20 wt % of the total carrier material. Variations from this composition such as a lower phosphoric acid content are possible. Further details as to the composition and production of SPA catalysts may be obtained from U.S. Pat. No. 3,050,472, U.S. Pat. No. 3,050,473 and U.S. Pat. No. 3,132,109. Feed to the oligomerization reactor zone 140 containing SPA catalyst should be kept dry except in an initial start-up phase.

The oligomerization reaction conditions in the oligomerization reactors 138, 150 in the oligomerization reactor zone 140 are set to keep the reactant fluids in the liquid phase. With liquid oligomerate recycle, lower pressures are necessary to maintain liquid phase. Operating pressures include between about 2.1 MPa (300 psia) and about 10.5 MPa (1520 psia), suitably at a pressure between about 2.1 MPa (300 psia) and about 6.9 MPa (1000 psia) and preferably at a pressure between about 2.8 MPa (400 psia) and about 4.1 MPa (600 psia). Lower pressures may be suitable if the reaction is kept in the liquid phase.

For the zeolite catalyst, the temperature of the oligomerization reactor zone 140 expressed in terms of a maximum bed temperature is in a range between about 150° C. and about 300° C. If diesel oligomerate is desired, the maximum bed temperature should between about 200° C. and about 250° C. and preferably between about 215° or about 225° C. and about 245° C. or between about 220° and about 240° C. The space velocity should be between about 0.5 and about 5 hr$^{-1}$.

For the SPA catalyst, the oligomerization temperature in the oligomerization reactor zone 140 should be in a range between about 100° C. and about 250° C. and suitably between about 150° C. and about 200° C. The liquid hourly space velocity (LHSV) should be between about 0.5 and about 5 hr$^{-1}$.

Across a single bed of oligomerization catalyst, the exothermic reaction will cause the temperature to rise. Consequently, the oligomerization reactor should be operated to allow the temperature at the outlet to be over about 25° C. greater than the temperature at the inlet.

The oligomerization reactor zone 140 with the oligomerization catalyst can be run in high conversion mode of greater than 95% conversion of feed olefins to produce a high quality diesel product and gasoline product. Normal butene conversion can exceed about 80%. Additionally, normal pentene conversion can exceed about 80%.

We have found that when $C_5$ olefins are present in the oligomerization feed stream, they dimerize or co-dimerize with other olefins, but tend to mitigate further oligomerization over the zeolite with a 10-ring uni-dimensional pore structure. Best mitigation of further oligomerization occurs when the $C_5$ olefins comprise between 15 or 30 and 70 wt % and preferably between 20 or 40 and 50 or 60 wt % of the olefins in the oligomerization feed. Consequently, the oligomerate stream in oligomerate conduit 156 may comprise less than about 80 wt % $C_9+$ hydrocarbons when $C_5$ olefins are present in the oligomerization feed at these proportions. Moreover, said oligomerate may comprise less than about 60 wt % $C_{12}+$ hydrocarbons when $C_5$ olefins are present in the oligomerization feed at these proportions. Furthermore, the net gasoline yield may be at least about 40 wt % when $C_5$ olefins are present in the oligomerization feed.

If diesel is desired, however, the oligomerization zone with the oligomerization catalyst can be operated to oligomerize light olefins; i.e., $C_4$ olefins, to distillate-range material by over 70 wt % yield per pass through the oligomerization reactor zone 140. In an aspect, at least about 70 wt % of the olefins in the oligomerization feed convert to $C_9+$ product oligomers boiling above about 150° C. (302° F.) cut point in a single pass through the oligomerization zone. The $C_{12}+$ oligomer from the oligomerization zone boiling above about 200° C. (392° F.) may have a cetane of at least 30 and preferably at least 40.

The composition of the oligomerate in oligomerate line 156 may be an olefinic hydrocarbon composition having $C_8$ olefins. The olefinic hydrocarbon composition may include gasoline. In an embodiment, the composition may be moderate in Type 2 disubstituted olefins and high in Type 4 trisubstituted olefins. In an aspect, the oligomerate composition may have a ratio of Type 2 disubstituted $C_8$ olefins to Type 1 monosubstituted $C_8$ olefins of greater than about 2. In a further aspect, a fraction of Type 2 disubstituted $C_8$ olefins in the total $C_8$ olefins in the oligomerate may be no less than about 7 and less than about 18 wt %. In an even further aspect, a fraction of Type 4 trisubstituted $C_8$ olefins in the total $C_8$ olefins may be no less than about 40 wt %. In a still further aspect, an average branch per $C_8$ hydrocarbon molecule in the oligomerate may be less than 2. The oligomerate may have a cetane of greater than 30 and preferably greater than 40. The oligomerate may have a density of less than 0.83 kg/m$^3$, preferably less than 0.81 kg/m$^3$, less than 20 ppmw sulfur or less than 1 vol % aromatics. The oligomerate may have a ratio of trimethyl pentene to the total $C_8$ olefins of no more than 50 and preferably no more than 40.

An oligomerization recovery zone 200 is in downstream communication with the oligomerization zone 130 and the oligomerate conduit 156. The oligomerate conduit 156 removes the oligomerate stream from the oligomerization zone 130.

The oligomerization recovery zone 200 may include a debutanizer column 210 which separates the oligomerate stream between vapor and liquid into a first vaporous oligomerate overhead light stream comprising $C_4$ olefins and hydrocarbons in a first overhead line 212 and a first liquid oligomerate bottom stream comprising $C_5+$ olefins and hydrocarbons in a first bottom line 214. When maximum production of distillate is desired, either to obtain diesel product or to recrack the diesel in the FCC zone 20 to make more propylene, the overhead pressure in the debutanizer column 210 may be between about 300 and about 350 kPa (gauge) and the bottom temperature may be between about 250° and about 300° C. When maximum production of gasoline is desired, the overhead pressure in the debutanizer column 210 may be between about 525 and about 575 kPa (gauge) and the bottom temperature may be between about 90° and about 140° C. The first vaporous oligomerate overhead light stream comprising $C_4$ hydrocarbons may be rejected from the process and subjected to further processing to recover useful components.

It is desired to maintain liquid phase in the oligomerization reactors. This is typically achieved by saturating product olefins and recycling them to the oligomerization reactor as a liquid. However, if olefinic product is being recycled to either the FCC zone 20 or the oligomerization zone 130, saturating olefins would inactivate the recycle feed. The oligomerization zone 130 can only further oligomerize olefinic recycle and the FCC zone 20 prefers olefinic feed to be further cracked to form propylene.

Liquid phase may be maintained in the oligomerization zone 130 by incorporating into the feed a $C_5$ stream from the oligomerization recovery zone 200. The oligomerization recovery zone 200 may include a depentanizer column 220 to which the first liquid oligomerate bottom stream comprising $C_5+$ hydrocarbons may be fed in line 214. The depentanizer column 220 may separate the first liquid oligomerate bottom stream between vapor and liquid into an intermediate stream comprising $C_5$ olefins and hydrocarbons in an intermediate line 222 and a liquid oligomerate bottom product stream comprising $C_6+$ olefins in a bottom product line 224. When maximum production of distillate is desired, either to obtain diesel product or to recrack the diesel in the FCC zone 20 to make more propylene, the overhead pressure in the depentanizer column 220 may be between about 10 and about 60 kPa (gauge) and the bottom temperature may be between about 225° and about 275° C. When maximum production of gasoline is desired, the overhead pressure in the depentanizer column 220 may be between about 250 and about 300 kPa (gauge) and the bottom temperature may be between about 150° and about 200° C.

The intermediate stream in intermediate line 222 may comprise at least 30 wt % and suitably at least 40 wt % $C_5$ hydrocarbons which can then act as a solvent in the oligomerization reactor zone 140 to maintain liquid phase therein. The overhead intermediate stream comprising $C_5$ hydrocarbons should have less than 10 wt % $C_4$ or $C_6$ hydrocarbons and preferably less than 1 wt % $C_4$ or $C_6$ hydrocarbons.

The intermediate stream may be condensed and recycled to the oligomerization zone 130 as a first intermediate recycle stream in an intermediate recycle line 226 to maintain the liquid phase in the oligomerization reactors 138, 150 operating in the oligomerization zone 130. The $C_5$ overhead stream may comprise $C_5$ olefins that can oligomerize in the oligomerization zone. The $C_5$ hydrocarbon presence in the oligomerization zone maintains the oligomerization reactors at liquid phase conditions. The pentanes are easily separated from the heavier olefinic product such as in the depentanizer column 220. The pentane recycled to the oligomerization zone also dilutes the feed olefins to help limit the temperature rise within the reactor due to the exothermicity of the reaction.

We have found that dimethyl sulfide boils with the $C_5$ hydrocarbons and deactivates the unidimensional, 10-ring pore structured zeolite which may be the oligomerization catalyst. The mercaptan extraction unit 112 does not remove sufficient dimethyl sulfide to avoid deactivating the oligomerization catalyst. Consequently, recycle of $C_5$ hydrocarbons to the oligomerization reactor zone 140 with oligomerization catalyst should be avoided by keeping valve 226' shut unless dimethyl sulfide can be successfully removed from the oligomerate stream or the oligomerization catalyst is not a unidimensional, 10-ring pore structured zeolite. However, the dimethyl sulfide does not substantially harm the solid phosphoric acid catalyst, so recycle of $C_5$ hydrocarbons to the oligomerization reactor zone 140 is suitable if SPA is the oligomerization catalyst.

In an aspect, the intermediate stream in the intermediate line 222 comprising $C_5$ hydrocarbons may be split into a purge stream in purge line 228 and the first intermediate recycle stream comprising $C_5$ hydrocarbons in the first intermediate recycle line 226. In an aspect, the first intermediate recycle stream in first intermediate recycle line 226 taken from the intermediate stream in intermediate line 222 is recycled to the oligomerization zone 130 downstream of the selective hydrogenation reactor 116. The intermediate stream in intermediate line 222 and the first intermediate recycle stream in intermediate recycle line 226 should be understood to be condensed overhead streams. The intermediate recycle stream comprising $C_5$ hydrocarbons may be recycled to the oligomerization zone 130 at a mass flow rate which is at least as great as and suitably no greater than three times the mass flow rate of the oligomerization feed stream in the oligomerization feed line 128 fed to said oligomerization zone 130 absent the addition of any recycle streams such as in line 246 to be explained hereinafter. The recycle rate may be adjusted as necessary to maintain liquid phase in the oligomerization reactors and to control temperature rise, and to maximize selectivity to gasoline range oligomer products.

The purge stream comprising $C_5$ hydrocarbons taken from the intermediate stream may be purged from the process in line 228 to avoid $C_5$ build up in the process. The purge stream comprising $C_5$ hydrocarbons in line 228 may be subjected to further processing to recover useful components or be blended in the gasoline pool.

Three streams may be taken from the liquid oligomerate bottom product stream in bottom product line 224. A recycle oligomerate product stream comprising $C_6+$ olefins in recycle oligomerate product line 230 may be taken from the liquid oligomerate bottom product stream in bottom product line 224. The liquid oligomerate bottom product stream in the bottom product line 224 may have the same composition as described for the $C_8$ olefins of the oligomerate in oligomerate line 156. The liquid oligomerate bottom product stream in the bottom product line 224 may have greater than 10 wt % $C_{10}$ isoolefins. Flow through recycle line 230 can be regulated by control valve 230'. In another aspect, a distillate separator feed stream in distillate feed line 232 may be taken from the liquid oligomerate bottom product stream in the bottom product line 224. Flow through distillate feed line 232 can be regulated by control valve 232'. In a further aspect, a gasoline oligomerate product stream in a gasoline oligomerate product line 250 can be taken from the liquid oligomerate bottom product stream in bottom product line 224. Flow through gasoline oligomerate product line 250 can be regulated by control valve 250'. Flow through recycle oligomerate product line 230, distillate feed line 232 and gasoline oligomerate product line 250 can be regulated by control valves 230', 232' and 250', respectively, such that flow through each line can be shut off or allowed irrespective of the other lines.

In an embodiment designed to bolster production of heavier oligomerate and maintain liquid phase conditions in the oligomerization reactor zone 140, an oligomerate return stream in oligomerate return line 231 may be taken from the recycle oligomerate product stream comprising $C_6+$ olefins in the recycle oligomerate product line 230 and be recycled to the oligomerization reactor zone 140 comprising oligomerization catalyst. In this case, a control valve 231' on oligomerate return line 231 is open, so that recycle oligomerate product is recycled to the oligomerization reactor zone 140 in the oligomerization zone 130. The oligomerization catalyst is resistant to excess oligomerization of heavier olefins, so recycling heavier olefins to the oligomerization catalyst will not result in excess oligomerization to heavier olefins than diesel. The recycle oligomerate product stream comprising $C_6+$ olefins serves to maintain liquid phase in the oligomerization reactor zone 140 and provides olefins that can oligomerize to heavier diesel range olefins. In this embodiment, the oligomerization zone 130 is in downstream communication with the first bottom line 214 of the debutanizer column 210 and the bottom product line 224 of the depentanizer column 220. In a further aspect, the recycle oligomerate product line 230 and the oligomerate return line 231 are in downstream communication with the oligomerization zone 130. Consequently, the oligomerization zone 130 is in upstream and downstream communication with the first bottom line 214, the bottom product line 224, the recycle oligomerate product line 230 and the oligomerate return line 231.

The concentration of dimethyl sulfide in the oligomerate return stream in the oligomerate return line 231 should be no more than 5 wppm sulfur as dimethylsulfide. Consequently, if the recycle oligomerate product stream in recycle oligomerate product line 230 is taken from the oligomerate bottom product stream comprising $C_6+$ olefins in the bottom product line 224 to be recycled to the oligomerization reactor zone 140, it should comprise no more than 5 wppm sulfur as dimethyl sulfide. Accordingly, the oligomerization recovery zone 200 should be operated to produce an oligomerate bottom product stream that has no more than 5 wppm sulfur as dimethyl sulfide and/or less than 1 wt % $C_5$ hydrocarbons.

If a refiner desires to make additional propylene in the FCC unit, an embodiment may be used in which an FCC recycle oligomerate stream taken from the recycle oligomerate product stream in the recycle oligomerate product line 230 from the oligomerate bottom product stream comprising $C_6+$ olefins in the bottom product line 224 may be recycled to the FCC recycle line 280. An FCC recycle oligomerate line 233 may take an FCC recycle oligomerate stream from the recycle oligomerate stream in recycle oligomerate line 230 and forward it to the FCC zone 20 through FCC recycle line 280. The FCC recycle oligomerate line 233 communicates the recycle oligomerate line with FCC recycle line 280 and the FCC reaction zone 20. A control valve 233' on the FCC recycle oligomerate line 233 may be open if recycle oligomerate product to the FCC zone 20 is desired. The FCC recycle line 280 will carry the FCC recycle oligomerate stream as feed to the FCC zone 20. In an aspect, the recycle oligomerate product stream in the recycle oligomerate product line 230 is in downstream communication with the FCC recovery zone 200. In a further aspect, the FCC recycle oligomerate line 233 is in downstream communication with the oligomerization zone 130. Hence, in an aspect, the FCC reaction zone 20 is in upstream and downstream communication with oligomerization zone 130 and/or FCC recovery zone 100. In a still further aspect, FCC recycle oligomerate line 233 and recycle oligomerate product line 230 are in upstream communication with the FCC reaction zone 20 to recycle oligomerate for fluid catalytic cracking down to propylene or other light olefins. One or both of valves 231' and 233' may be opened or closed depending on the refiner's desire for recycle to the oligomerization zone 130 or the FCC zone 20, respectively.

In an embodiment in which the oligomerization catalyst is SPA in the oligomerization reactor zone 140 for oligomerizing $C_4$ olefins or a mixed $C_4$ and $C_5$ olefin stream, we have found that a gasoline product stream can be provided by the oligomerate bottom product stream in bottom product line 224. The SPA catalyst minimizes the formation of $C_{12}+$ species with either a $C_4$ olefin or $C_4$ and $C_5$ olefin feed. Consequently, even when heavier olefins than $C_4$ olefins are present in the oligomerization feed stream, the SPA catalyst manages to keep $C_{12}+$ olefins present in the liquid oligomerate bottom product stream in the bottom product line 224 below less than about 20 wt % even when over 85 wt % of feed olefins are converted and particularly when over 90 wt % of $C_4$ olefins are converted to oligomerate.

Accordingly, the liquid oligomerate bottom product stream in bottom product line 224 provides gasoline range material that meets the Engler T90 gasoline specification of 193° C. (380° F.) using the ASTM D-86 Test Method without further treatment when SPA is the second oligomerization catalyst in the oligomerization reactor zone 140. That is, 90 wt % of the resulting liquid oligomerate bottom product stream, for example, in bottom product line 224 will boil before its temperature is raised to 193° C. (380° F.). Consequently, a gasoline oligomerate product stream can be collected from the liquid oligomerate bottom product stream in a gasoline oligomerate product line 250 and blended in the gasoline pool without further treatment such as separation or chemical upgrading. The gasoline oligomerate product line 250 may be in upstream communication with a gasoline tank 252 or a gasoline blending line of a gasoline pool. However, further treatment such as partial or full hydrogenation to reduce olefinicity may be contemplated. In such a case, control valves 232' and 230' may be all or partially closed and control valve 250' on oligomerate liquid product line 250 may be opened to allow $C_6+$ gasoline product to be sent to the gasoline tank 252 or the gasoline blending line.

The oligomerization recovery zone 200 may also include a distillate separator column 240 to which the distillate separator oligomerate feed stream comprising oligomerate $C_6+$ hydrocarbons may be fed in distillate feed line 232 taken from the liquid oligomerate bottom product stream in line 224 for further separation. The distillate separator column 240 is in downstream communication with the first bottom line 214 of the debutanizer column 210 and the bottom product line 224 of the depentanizer column 220.

The distillate separator column 240 separates the distillate separator oligomerate feed stream into an gasoline overhead stream in an overhead line 242 comprising $C_6$, $C_7$, $C_8$, $C_9$, $C_{10}$ and/or $C_{11}$ olefins and a bottom distillate stream comprising $C_8+$, $C_9+$, $C_{10}+$, $C_{11}+$, or $C_{12}+$ olefins in a diesel bottom line 244. When maximum production of distillate is desired, either to obtain diesel product or to recrack the diesel in the FCC zone 20 to make more propylene, the overhead pressure in the distillate separator column 240 may be between about 10 and about 60 kPa (gauge) and the bottom temperature may be between about 225° and about 275° C. When maximum production of gasoline is desired, the overhead pressure in the distillate separator column 240 may be between about 10 and about 60 kPa (gauge) and the bottom temperature may be between about 190° and about 250° C. The bottom temperature can be adjusted between about 175° and about 275° C. to adjust the bottom product between a $C_9+$ olefin cut and a $C_{12}+$ olefin cut based on the heaviness of the diesel cut desired by the refiner. The gasoline overhead stream in gasoline overhead line 242 may have the same composition as described for the $C_8$ olefins of the oligomerate in oligomerate line 156. The diesel bottoms stream in diesel bottoms line 244 may have greater than 30 wt % $C_9+$ isoolefins.

For refiners who are interested in distillate production at a particular time, the gasoline overhead stream comprising $C_8$ olefins in the gasoline overhead line 242 of the distillate separator column can be recycled to the oligomerization zone 130 to increase the production of distillate. For example, a gasoline overhead recycle stream in gasoline overhead recycle line 246 may be taken from the gasoline overhead stream in gasoline overhead line 242 and mixed with the fresh oligomerization feed stream in oligomerization feed line 128. A control valve 246' may be used to completely shut off flow through gasoline overhead recycle line 246 or allow partial or full flow therethrough. The gasoline overhead recycle line 246 may be in downstream communication with the oligomerization recovery zone 200 to generate diesel range material.

Preferably, the gasoline recycle gasoline stream in line 246, which may be taken from the gasoline overhead in line 242, may be recycled to the oligomerization reactors, 138 and 150 of the oligomerization reactor zone 140 with oligomerization catalyst. The gasoline overhead stream may comprise $C_6$-$C_{11}$ olefins and preferably $C_7$-$C_9$ olefins and most preferably $C_8$ olefins that can oligomerize with $C_4$-$C_5$ olefins in the oligomerization feed stream in the oligomerization zone 130 to diesel range material comprising $C_{10}$-$C_{16}$ diesel product. $C_4$ olefins continue to oligomerize with $C_4$ olefins and $C_5$ olefins if present in the feed.

The oligomerization catalyst, and particularly, the uni-dimensional, 10-ring pore structured zeolite, converts a significant fraction of the gasoline-range olefins, such as $C_8$ olefins, to distillate material by oligomerizing them with feed olefins, such as $C_4$ and/or $C_5$ olefins. Additionally, the presence of the gasoline-range olefins also encourages oligomerization of the feed olefins with each other over the zeolite catalyst. Surprisingly, the isobutene conversion is lower than normal butene conversion at high overall butene conversion such as over 90% $C_4$ olefin conversion. When gasoline is recycled from the gasoline overhead line 242 to the oligomerization reactor zone 140 for oligomerization over uni-dimensional, 10-ring pore structured zeolite, oligomerate from the oligomerization zone in oligomerate line 156 may comprise greater than 30 wt % $C_9+$ olefins. Under these circumstances, oligomerate from the oligomerization reactor zone in oligomerate line 156 may comprise greater than 50 wt % or even greater than 60 wt % $C_9+$ olefins.

In an aspect, the gasoline overhead stream in gasoline overhead line 242 may be recovered as product in product gasoline line 248 in downstream communication with the recovery zone 200. A control valve 248' may be used to completely shut off flow through gasoline product line 248 or allow partial or full flow therethrough. The gasoline product stream may be subjected to further processing to recover useful components or blended in the gasoline pool. The gasoline product line 248 may be in upstream communication with a gasoline tank 252 or a gasoline blending line of a gasoline pool. In this aspect, the overhead line 242 of the distillate separator column may be in upstream communication with the gasoline tank 252 or the gasoline blending line.

In an embodiment, the diesel bottom stream in a diesel bottom line 244 may be recycled to the FCC zone 20 in FCC recycle line 280 via a recycle diesel line 260 in downstream communication with the oligomerization recovery zone 200 to be cracked to propylene product in the FCC zone. A recycle diesel bottom stream in recycle diesel line 260 taken from the diesel bottom stream in line 244 may be forwarded to the FCC recycle line 280. The diesel bottom stream may comprise $C_9+$, $C_{10}+$, $C_{11}+$ or $C_{12}+$ olefins that can crack to propylene. A control valve 260' may be used to completely shut off flow through recycle diesel line 260 or allow partial or full flow therethrough. In this embodiment, the FCC zone 20 is in downstream communication with the distillate separator column 240 and particularly the diesel bottom line 244.

If the FCC zone 20 comprises a single reactor riser 26, the first reactor riser 26 may be in downstream communication with the hydrocarbon feed line 24 and the diesel bottom line 244 of the distillate separator column 240. If the FCC zone 20 comprises the first reactor riser 26 and a second reactor riser 74, the first reactor riser 26 may be in downstream communication with the hydrocarbon feed line 24 and the second reactor riser 74 may be in downstream communication with the bottom line 244 of the distillate separator column 240.

We have found that $C_6+$ oligomerate and distillate oligomerate subjected to FCC is converted best over a blend of medium or smaller pore zeolite blended with a large pore zeolite such as Y zeolite as explained previously with respect to the FCC zone 20. Additionally, oligomerate produced over the oligomerization catalyst in the oligomerization reactor zone 140 provides an excellent feed to the FCC zone that can be cracked to yield greater quantities of propylene.

In an aspect, the diesel bottom stream may be recovered as product in a diesel product line 262 in downstream communication with the oligomerization recovery zone 200. The diesel product line in line 262 is taken from the diesel bottom stream in diesel bottom line 244. A control valve 262' may be used to completely shut off flow through the diesel product line 262 or allow partial or full flow therethrough. The diesel product stream may be subjected to further processing to recover useful components or blended in the diesel pool. The diesel product line 262 may be in upstream communication with a diesel tank 264 or a diesel blending line of a diesel pool. Additionally, LCO from LCO line 107 may also be blended with diesel in diesel product line 262.

Figure 2:
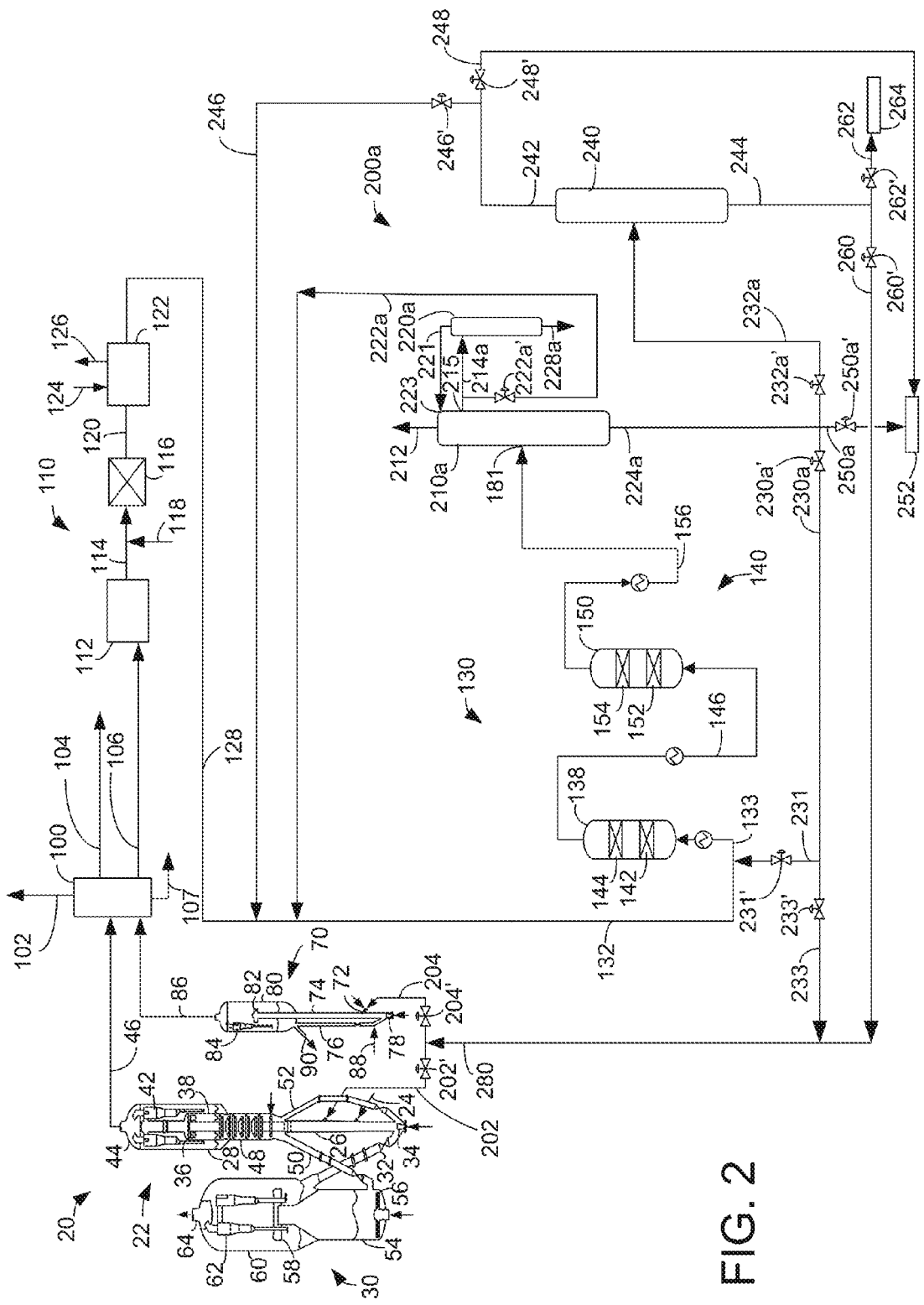
FIG. 2 is an alternative schematic drawing of the present invention.

FIG. 2 depicts an alternative embodiment of the oligomerization recovery zone 200. Elements in FIG. 2 with the same configuration as in FIG. 1 will have the same reference numeral as in FIG. 1. Elements in FIG. 2 which have a different configuration as the corresponding element in FIG. 1 will have the same reference numeral but designated with a suffix "a". The configuration and operation of the embodiment of FIG. 2 is essentially the same as in FIG. 1 with the exceptions noted below.

In FIG. 2, the oligomerization recovery zone 200a comprises a fractionation debutanizer column 210a in downstream communication with the oligomerization zone 130. The oligomerate steam in oligomerate line 156 is fed to an inlet 181 to the fractionation debutanizer column 210a which separates the oligomerate stream between vapor and liquid into a first vaporous oligomerate overhead light stream in a first overhead line 212 comprising $C_4$ hydrocarbons, an intermediate side stream in intermediate line 214a comprising $C_5$ hydrocarbons and a liquid oligomerate bottom product stream comprising $C_6+$ olefins in a bottom product line 224a. The intermediate side stream may be taken from a side outlet 215 of the fractionation debutanizer column 210a. The intermediate stream may be a liquid collected on a tray in the fractionation debutanizer column 210a.

The fractionation debutanizer column 210a feeds the intermediate side stream from the side outlet 215 of the fractionation debutanizer column 210a to a side stripper column 220a to separate the intermediate side stream into a second overhead stream in second overhead line 221 comprising $C_4$-hydrocarbons and a second bottom stream in a second bottom line 228a comprising $C_5$ hydrocarbons. The side stripper column 220a may be in downstream communication with the side outlet 215 of the fractionation debutanizer column 210a. The second overhead stream 221 is fed to the fractionation debutanizer column 210a at a side inlet 223. Consequently, the fractionation debutanizer column 210a is in downstream communication with the overhead line 221 from the side stripper column 220a. Hence, in an aspect, the fractionation debutanizer column 210a is in upstream and downstream communication with the side stripper column 220a.

The feed inlet 181 to the fractionation debutanizer column may be at a lower elevation than a side inlet 223 from the overhead line 221 from the side stripper 220a. Additionally, the side inlet 223 from the overhead line 221 from the side stripper 220a may be at a higher elevation than the side outlet 215. Lastly, the side outlet 215 may be at a higher elevation on the debutanizer column 210a than the feed inlet 181.

When maximum production of distillate is desired, either to obtain diesel product or to recrack the diesel in the FCC zone 20 to make more propylene, the overhead pressure in the debutanizer column 210a may be between about 350 and about 400 kPa (gauge) and the bottom temperature may be between about 270° and about 320° C. When maximum production of gasoline is desired, the overhead pressure in the debutanizer column 210a may be between about 350 and about 400 kPa (gauge) and the bottom temperature may be between about 170° and about 220° C. The side stripper column 220a may have an overhead pressure of between about 400 and about 450 kPa and a bottom temperature of between about 60° and about 115° C. in both modes.

One or both of the first vaporous oligomerate overhead light stream in first overhead line 212 comprising $C_4$ hydrocarbons and the second bottom stream in second bottom line 228a comprising $C_5$ hydrocarbons may be purged from the process.

A stream comprising $C_5$ hydrocarbons may be used to maintain the oligomerization zone 130 in liquid phase and provide additional $C_5$ olefins for oligomerization. An intermediate stream comprising $C_5$ hydrocarbons in intermediate line 222a may be taken from the intermediate side stream in line 214a before it is further fractionated such as in the side stripper 220a and recycled to the oligomerization zone 130 through an open control valve 222a' thereon. Taking a stream of $C_5$ hydrocarbons from the intermediate side stream removes a large amount of material from the side stripper column 220a without requiring it to be further reboiled or condensed thus decreasing its capacity and the expense to operate. Accordingly, the oligomerization zone 130 is in downstream communication with said side outlet 215.

A recycle oligomerate stream comprising $C_6+$ olefins may be used to maintain the oligomerization zone 130 in liquid phase and provide additional olefins for oligomerization. A recycle oligomerate product stream may be taken in recycle oligomerate product line 230a through open control valve 230a' from the liquid oligomerate bottom product stream in the bottom product line 224a which comprises $C_6+$ olefins. An oligomerate return stream in oligomerate return line 231 through open control valve 231' may be taken from the recycle oligomerate product stream in recycle oligomerate product line 230a and be recycled to the oligomerization zone 130. The oligomerization zone 130 may be, therefore, in downstream communication with the bottom product line 224a of the fractionation column. The oligomerate return stream in oligomerate return line 231 may be recycled to the oligomerization reactor zone 140 having the oligomerization catalyst.

Distillate oligomer product may be recycled to the FCC unit to make more propylene. An FCC recycle oligomerate stream in FCC recycle oligomerate line 233 may be taken from the recycle oligomerate product stream in recycle oligomerate product line 230a and be forwarded through open valve 233' to the FCC zone 20 in FCC recycle line 280. Accordingly, the FCC zone may be in downstream communication with the bottom product line 224a of the fractionation debutanizer column. Hence, in an aspect, the FCC zone 20 may be in upstream and downstream communication with the oligomerization zone 130 and/or the debutanizer column 210a.

If the oligomerate bottom product stream has a suitable composition, it may be taken as gasoline product in line 250a through control valve 250a' to a gasoline pool which may comprise a gasoline tank 252 or a gasoline blending line. Accordingly, the gasoline tank 252 or the gasoline blending line may be in downstream communication with an oligomerate bottom product line 224a of said fractionation debutanizer column 210a.

If sufficient diesel is provided in bottom product line 224a, the gasoline should be separated from the diesel. A distillate separator feed stream may be taken from the oligomerate bottom product stream in bottom product line 224a in line 232a through open control valve 232a' to a distillate separator column 240. The distillate separator column 240 can separate the distillate separator feed stream into a gasoline stream 242 and a distillate stream 244 as previously described with respect to FIG. 1. Accordingly, the distillate separator column 240 is in downstream communication with a bottom product line of said fractionation debutanizer column 210a.

In the embodiment of FIG. 2, when maximum production of distillate is desired, either to obtain diesel product or to recrack the diesel in the FCC zone 20 to make more propylene, the overhead pressure in the distillate separator column 240 may be between about 150 and about 200 kPa (gauge) and the bottom temperature may be between about 250° and about 300° C. When maximum production of gasoline is desired, the overhead pressure in the debutanizer column 210 may be between about 150 and about 200 kPa (gauge) and the bottom temperature may be between about 210° and about 260° C.

The invention will now be further illustrated by the following non-limiting examples.

EXAMPLES

Example 1

Feed 1 in Table 2 was contacted with four catalysts to determine their effectiveness in oligomerizing butenes.

TABLE 2

| Component | Fraction, wt % |
|---|---|
| propylene | 0.1 |
| Iso-$C_4$'s | 70.04 |
| isobutylene | 7.7 |
| 1-butene | 5.7 |
| 2-butene (cis and trans) | 16.28 |
| 3-methyl-1-butene | 0.16 |
| acetone | 0.02 |
| Total | 100 |

Catalyst A is an MTT catalyst purchased from Zeolyst having a product code Z2K019E and extruded with alumina to be 25 wt % zeolite. Of MTT zeolite powder, 53.7 grams was combined with 2.0 grams Methocel and 208.3 grams Catapal B boehmite. These powders were mixed in a muller before a mixture of 18.2 g $HNO_3$ and 133 grams distilled water was added to the powders. The composition was blended thoroughly in the muller to effect an extrudable dough of about 52% LOI. The dough then was extruded through a die plate to form cylindrical extrudates having a diameter of about 3.18 mm. The extrudates then were air dried, and calcined at a temperature of about 550° C. The MTT catalyst was not selectivated to neutralize surface acid sites such as with an amine.

Catalyst B is a SPA catalyst commercially available from UOP LLC.

Catalyst C is an MTW catalyst with a silica-to-alumina ratio of 36:1. Of MTW zeolite powder made in accordance with the teaching of U.S. Pat. No. 7,525,008 B2, 26.4 grams was combined with and 135.1 grams Versal 251 boehmite. These powders were mixed in a muller before a mixture of 15.2 grams of nitric acid and 65 grams of distilled water were added to the powders. The composition was blended thoroughly in the muller to effect an extrudable dough of about 48% LOI. The dough then was extruded through a die plate to form cylindrical extrudates having a diameter of about ⅟₃₂". The extrudates then were air dried and calcined at a temperature of about 550° C.

Catalyst D is an MFI catalyst purchased from Zeolyst having a product code of CBV-8014 having a silica-to-alumina ratio of 80:1 and extruded with alumina at 25 wt % zeolite. Of MFI-80 zeolite powder, 53.8 grams was combined with 205.5 grams Catapal B boehmite and 2 grams of Methocel. These powders were mixed in a muller before a mixture of 12.1 grams nitric acid and 115.7 grams distilled water were added to the powders. The composition was blended thoroughly in the muller, then an additional 40 grams of water was added to effect an extrudable dough of about 53% LOI. The dough then was extruded through a die plate to form cylindrical extrudates having a diameter of about 3.18 mm. The extrudates then were air dried, and calcined at a temperature of about 550° C.

Figure 3:
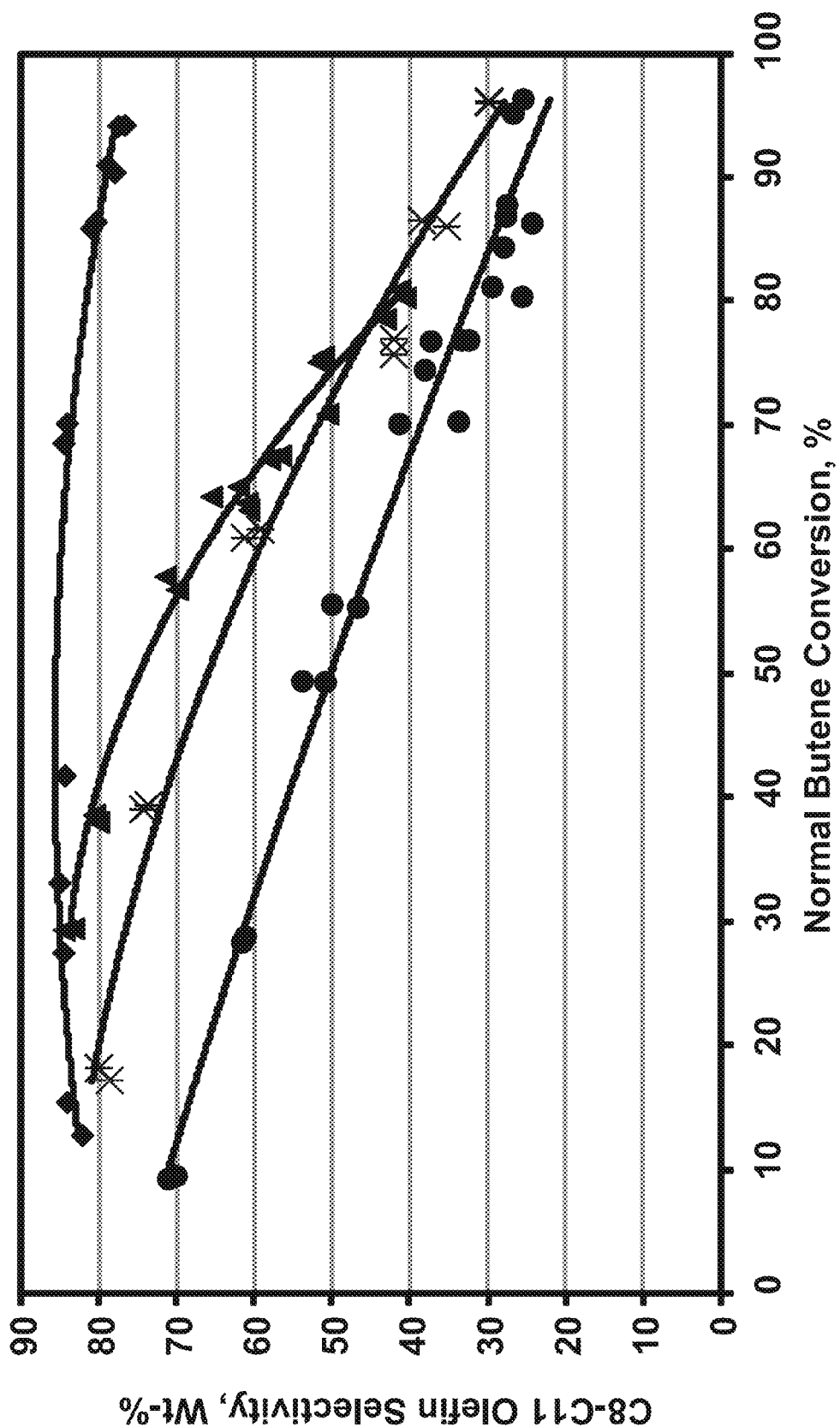
FIG. 3 is a plot of $C_8$-$C_{11}$ olefin selectivity versus normal butene conversion.
Figure 4:
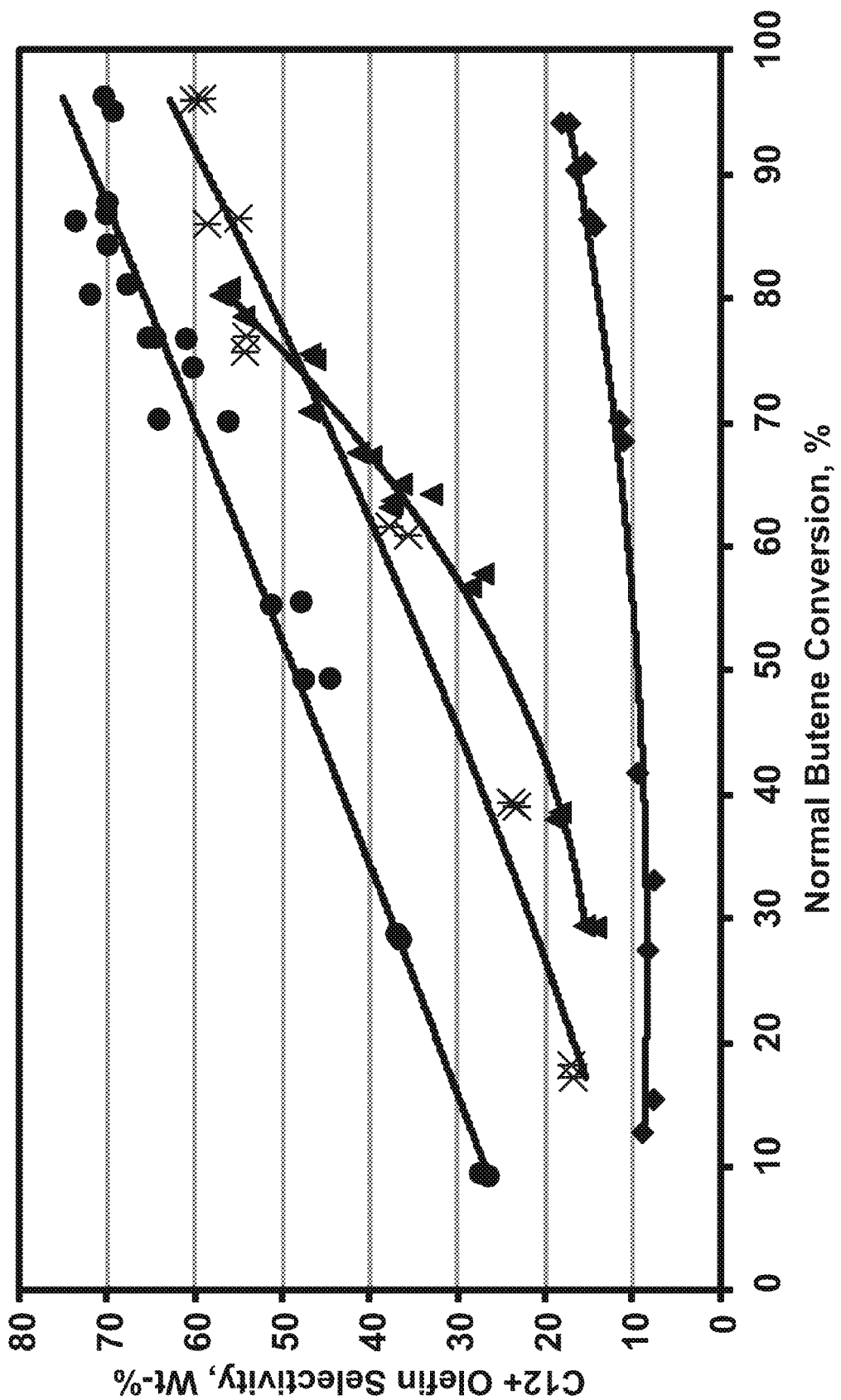
FIG. 4 is a plot of $C_{12}$+ olefin selectivity versus normal butene conversion.

The experiments were operated at 6.2 MPa and inlet temperatures at intervals between 160° and 240° C. to obtain different normal butene conversions. Results are shown in FIGS. 3 and 4. In FIG. 3, $C_8$ to $C_{11}$ olefin selectivity is plotted against normal butene conversion to provide profiles for each catalyst.

Table 3 compares the RONC ±3 for each product by catalyst and provides a key to FIG. 3. The SPA catalyst B is superior, but the MTT catalyst A is the least effective in producing gasoline range olefins.

TABLE 3

| | Catalyst | | RONC |
|---|---|---|---|
| A | MTT | circles | 92 |
| B | SPA | diamonds | 96 |
| C | MTW | triangles | 97 |
| D | MFI-80 | asterisks | 95 |

The SPA catalyst was able to achieve over 95 wt % yield of gasoline having a RONC of >95 and with an Engler T90 value of 185° C. for the entire product. The T-90 gasoline specification is less than 193° C.

In FIG. 4, $C_{12}+$ olefin selectivity is plotted against normal butene conversion to provide profiles for each catalyst. Table 4 compares the derived cetane number ±2 for each product by catalyst and provides a key to FIG. 4.

TABLE 4

| | Catalyst | | Cetane |
|---|---|---|---|
| A | MTT | circles | 41 |
| B | SPA | diamonds | <14 |
| C | MTW | triangles | 28 |
| D | MFI-80 | asterisks | 36 |

FIG. 4 shows that the MTT catalyst provides the highest $C_{12}+$ olefin selectivity which reaches over 70 wt %. These selectivities are from a single pass of the feed stream through the oligomerization reactor. Additionally, the MTT catalyst provided $C_{12}+$ oligomerate with the highest derived cetane. Cetane was derived using ASTM D6890 on the $C_{12}+$ fraction at the 204° C. (400° F.) cut point. Conversely to gasoline selectivity, the MTT catalyst A is superior, but the SPA catalyst B is the least effective in producing diesel range olefins.

The MTT catalyst was able to produce diesel with a cetane rating of greater than 40. The diesel cloud point was determined by ASTM D2500 to be −66° C. and the T90 was 319° C. using ASTM D86 Method. The T90 specification for diesel in the United States is between 282 and 338° C., so the diesel product meets the U.S. diesel standard.

Example 2

A comprehensive two-dimensional gas chromatography with flame ionization detection (GCxGC-FID) method was developed and utilized to analyze the composition of light olefin oligomerization product streams. To develop the peak identifications, a GCxGC instrument equipped with a time of flight mass spectrometer (TOFMS) was used. Peak identifications were checked against a table of $C_8$ olefin boiling points for consistency and by performing GC-FID of the olefinic sample with and without hydrogenation catalyst in the GC inlet to ensure that peaks assigned to a particular $C_8$ mono-olefin moved to their respective saturated $C_8$ isoparaffins. The identification of $C_8$ paraffin isomers can be achieved using the UOP690 method. Careful matching of chromatographic conditions between GCxGC-FID and GCxGC-TOFMS allows one to translate identifications made from the TOFMS analysis to the GCxGC-FID for quantitative analysis. The following 48 compounds in the $C_8$ region were identified and quantified:

$C_8$ olefin species identified are listed as follows: 2,3-dimethyl-2-butene, 3,4-dimethyl-2-pentene, 3,4-dimethyl-2-pentene, 2,4,4-trimethyl-1-pentene, 2,2-dimethyl-trans-3-hexene, 2,5-dimethyl-3-hexene, 3,3-dimethyl-1-hexene, 3,4,4-trimethyl-1-pentene, 2,4,4-trimethyl-2-pentene, 4,4-dimethyl-2-hexene, 4,4-dimethyl-1-hexene, 2,3,4-trimethyl-1-pentene, 2,3,3-trimethyl-1-pentene, 2,4-dimethyl-trans-3-hexene, 2,4-dimethyl-cis-3-hexene, 3,3-dimethyl-2-ethyl-1-butene, 2,4-dimethyl-1-hexene, 2,3-dimethyl-1-hexene, 2-methyl-3-heptene, 3,4,4-trimethyl-2-pentene, 2,5-dimethyl-2-hexene, 5-methyl-3-heptene, 3,5-dimethyl-2-hexene, 6-methyl-3-heptene, 4-methyl-1-heptene, 4-methyl-3-ethyl-trans-2-pentene, 2,3-dimethyl-3-hexene, 4-methyl-3-ethyl-cis-2-pentene, 3,4-dimethyl-2-hexene, 3-ethyl-3-hexene, 6-methyl-2-heptene, 2,3,4-trimethyl-2-pentene, 2-methyl-3-ethyl-2-pentene, 5-methyl-2-heptene, 2-n-propyl-1-pentene, 4-methyl-3-heptene, 2-ethyl-1-hexene, 2-methyl-1-heptene, 3-methyl-3-heptene, trans-3-octene, 2,3-dimethyl-2-hexene, 3-methyl-2-heptene, 3,4-dimethyl-trans-3-hexene, cis-3-octene, 2-methyl-2-heptene, trans-2-octene, cis-2-octene, and 3,4-dimethyl-cis-3-hexene.

$C_8$ olefins in the oligomerate produced by all four catalysts were evaluated by the GCxGC-FID method to characterize oligomerate product composite by olefin type. GCxGC analysis on the composite product of the experiment was used to compare the product olefinic isomers from Catalysts A and B as shown in Table 5.

TABLE 5

| Isomer Species | Fraction from Catalyst A, wt % | Fraction from Catalyst B, wt % |
|---|---|---|
| $C_5$ olefins | 0.02 | 3.12 |
| $C_6$ olefins | 1.50 | 0.25 |
| $C_7$ olefins | 1.13 | 0.92 |
| linear $C_8=$ | 0.91 | 0.03 |
| methyl-heptenes | 10.03 | 1.68 |
| dimethyl-hexenes | 13.25 | 18.70 |
| trimethyl-pentenes | 7.24 | 52.63 |
| $C_9$ olefins | 3.03 | 3.63 |
| $C_{10}$ olefins | 1.92 | 1.40 |
| $C_{11}$ olefins | 5.67 | 7.13 |
| $C_{12}$ olefins | 29.86 | 6.64 |
| $C_{13}$ olefins | 3.13 | 0.56 |
| $C_{14}$ olefins | 1.61 | 0.17 |
| $C_{15}$ olefins | 3.28 | 0.37 |
| $C_{16}$ olefins | 13.37 | 0.25 |
| $C_{17}$ olefins | 1.47 | 0.00 |
| $C_{18}$ olefins | 0.64 | 0.00 |
| $C_{19}$ olefins | 1.12 | 0.00 |
| Other Olefins and Polar Unknowns | 0.82 | 2.52 |
| Total | 100.00 | 100.00 |

Catalyst B, SPA, produces over 70 wt % $C_8$ olefins with over 70 wt % of the $C_8$ olefins being trimethyl pentenes. However, Catalyst A, MTT, produces only just over 31 wt % $C_8$ olefins of which only 23 wt % of the $C_8$ olefins are trimethyl pentenes. Catalyst A produced almost 30 wt % $C_{12}$ olefins. It is evident that MTT can produce a more linear and larger product from light olefins such as butene.

Comparisons are shown in Table 6. All percentages are in weight percent. "Composition Fraction" is the fraction of the species in the entire composition. "Olefin Fraction" is the fraction of the species among the $C_8$ olefins. "Average Branches" for the $C_8$ olefins is the average branches or alkyl groups per olefin molecule calculated by the ratio of the sum of the total weight of each isomer of branched $C_8$ olefins multiplied by the number of alkyl groups of that isomer in the composition divided by the total weight of normal octene, methyl heptene, dimethyl hexene and trimethyl pentene in the composition. "Olefin Isomer Fraction" is fraction of $C_8$ olefin isomer with the structure among all $C_8$ olefins. "TMP/$C_8$ Olefins" is the ratio of trimethyl pentene among linear octene, methyl heptene, dimethyl hexene and trimethyl pentene.

TABLE 6

| $C_8$ Olefin Species | Catalysts | | | |
|---|---|---|---|---|
| | A | B | C | D |
| Composition Fraction | | | | |
| Type I composition, % | 0.6 | 2.1 | 0.5 | 2.3 |
| Type II composition, % | 3.3 | 1.0 | 0.4 | 3.5 |
| Type III composition, % | 6.8 | 16.2 | 3.1 | 15.4 |
| Type IV composition, % | 14.0 | 14.6 | 3.7 | 21.4 |
| Type V composition, % | 4.8 | 19.5 | 3.8 | 13.9 |
| Total | 29.5 | 53.3 | 11.5 | 56.3 |
| Olefin Fraction | | | | |
| Type I olefin, % | 2.1 | 4.0 | 4.4 | 4.0 |
| Type II olefin, % | 11.3 | 1.8 | 3.4 | 6.1 |
| Type III olefin, % | 22.8 | 30.3 | 27.1 | 27.3 |
| Type IV olefin, % | 47.3 | 27.3 | 31.7 | 38.0 |
| Type V olefin, % | 16.3 | 36.6 | 33.4 | 24.7 |
| Total | 100 | 100 | 100 | 100 |
| Average Branches | 1.98 | 2.75 | 2.55 | 2.32 |
| $C_8$ Olefin Isomer Fraction | | | | |
| Linear octene, % | 2.8 | 0.0 | 0.1 | 0.7 |
| Methyl heptene, % | 27.3 | 2.1 | 5.1 | 11.9 |
| Dimethyl hexene, % | 34.9 | 20.0 | 32.9 | 38.7 |
| Trimethyl pentene, % | 31.3 | 75.4 | 59.2 | 44.4 |
| Other $C_8$ monoolefins, % | 3.8 | 2.5 | 2.8 | 4.4 |
| TMP/$C_8$ Olefins, % | 32.5 | 77.3 | 60.9 | 46.4 |

The fraction of Type 2 disubstituted $C_8$ olefins in the total $C_8$ olefins for Catalyst A was 11.3 wt % which was much higher than all the other catalysts. The ratio of Type 2 disubstituted $C_8$ olefins to Type 1 monosubstituted $C_8$ olefins for catalyst A was 5.3. All the other catalysts had the same ratio of less than one. The fraction of Type 4 trisubstituted $C_8$ olefins in the total $C_8$ olefins in the oligomerate for Catalyst A was 47 wt %. All of the other catalysts had the same fraction of no more than about 38 wt %. The average branch per hydrocarbon molecule for Catalyst A was 1.98; whereas, the other catalysts were all over 2. The ratio of trimethyl pentene to the total $C_8$ olefins in the oligomerate was 32.5; whereas all of the other catalysts had ratios over 46.

Example 3

Two types of feed were oligomerized over oligomerization catalyst A of Example 1, MTT zeolite. Feeds 1 and 2 contacted with catalyst A are shown in Table 7. Feed 1 is from Example 1.

TABLE 7

| Component | Feed 1 Fraction, wt % | Feed 2 Fraction, wt % |
|---|---|---|
| propylene | 0.1 | 0.1 |
| isobutane | 70.04 | 9.73 |
| isobutylene | 7.7 | 6.3 |
| 1-butene | 5.7 | 4.9 |

TABLE 7-continued

| Component | Feed 1 Fraction, wt % | Feed 2 Fraction, wt % |
|---|---|---|
| 2-methyl-2-butene | 0 | 9.0 |
| 2-butene (cis & trans) | 16.28 | 9.8 |
| 3-met-1-butene | 0.16 | 0.16 |
| n-hexane | 0 | 60 |
| acetone | 0.02 | 0.01 |
| Total | 100 | 100 |

In Feed 2, $C_5$ olefin is made up of 2-methyl-2-butene and 3-methyl-1-butene which comprises 9.16 wt % of the reaction mixture representing about a third of the olefins in the feed. 3-methyl-1-butene is present in both feeds in small amounts. Propylene was present at less than 0.1 wt % in both feeds.

The reaction conditions were 6.2 MPa and a 1.5 WHSV. The maximum catalyst bed temperature was 220° C. Oligomerization achievements are shown in Table 8.

TABLE 8

| | Feed 1 | Feed 2 |
|---|---|---|
| Inlet Temperature, ° C. | 192 | 198 |
| $C_4$ olefin conversion, % | 98 | 99 |
| $nC_4$ olefin conversion, % | 97 | 99 |
| $C_5$ olefin conversion, % | n/a | 95 |
| $C_5$-$C_7$ selectivity, wt % | 3 | 5 |
| $C_8$-$C_{11}$ selectivity, wt % | 26 | 40 |
| $C_{12}$-$C_{15}$ selectivity, wt % | 48 | 40 |
| $C_{16}$+ selectivity, wt % | 23 | 16 |
| Total $C_9$+ selectivity, wt % | 78 | 79 |
| Total $C_{12}$+ selectivity, wt % | 71 | 56 |
| Net gasoline yield, wt % | 35 | 44 |
| Net distillate yield, wt % | 76 | 77 |

Normal $C_4$ olefin conversion reached 99% with $C_5$ olefins in Feed 2 and was 97 wt % without $C_5$ olefins in Feed 1. $C_5$ olefin conversion reached 95%. With $C_5$ olefins in Feed 2, it was expected that a greater proportion of heavier, distillate range olefins would be made. However, the Feed 2 with $C_5$ olefins oligomerized to a greater selectivity of lighter, gasoline range product in the $C_5$-$C_7$ and $C_8$-$C_{11}$ range and a smaller selectivity to heavier distillate range product in the $C_{12}$-$C_{15}$ and $C_{16}$+ range.

This surprising result indicates that by adding $C_5$ olefins to the feed, a greater yield of gasoline can be made over Catalyst A, MTT. This is confirmed by the greater net yield of gasoline and the lower selectivity to $C_{12}$+ fraction for Feed 2 than for Feed 1. Also, but not to the same degree, by adding $C_5$ olefins to the feed, a greater yield of distillate range material can be made. This is confirmed by the greater net yield of distillate for Feed 2 than for Feed 1 on a single pass basis. Gasoline yield was classified by product meeting the Engler T90 requirement and distillate yield was classified by product boiling over 150° C. (300° F.).

Example 4

Three types of feed were oligomerized over oligomerization catalyst B of Example 1, SPA. The feeds contacted with catalyst B are shown in Table 9. Feed 2 is the same as Feed 2 in Example 3. Isooctane was used as a diluent with Feed 3 because it is expected to behave inertly just as isobutane. Feed 4 is similar to Feed 2 but has the pentenes evenly split between iso and normal pentenes, which is roughly expected to be found in an FCC product, and diluted with isobutane instead of hexane and isobutane.

TABLE 9

| Component | Feed 2 Fraction, wt % | Feed 3 Fraction, wt % | Feed 4 Fraction, wt % |
|---|---|---|---|
| propylene | 0.1 | 0.08 | 0.1 |
| 1,3-butadiene | 0 | 0.28 | 0 |
| isobutane | 9.73 | 6.45 | 69.72 |
| isobutylene | 6.3 | 7.30 | 6.3 |
| 1-butene | 4.9 | 5.07 | 4.9 |
| 2-methyl-2-butene | 9.0 | 0 | 4.5 |
| 2-butene (cis & trans) | 9.8 | 11.33 | 9.8 |
| 3-met-1-butene | 0.16 | 0.16 | 0.16 |
| 2-pentene | 0 | 0 | 4.5 |
| cyclopentane | 0 | 0.28 | 0 |
| n-hexane | 60 | 0 | 0 |
| isooctane | 0 | 60.01 | 0 |
| acetone | 0.01 | 0.01 | 0.02 |
| Total | 100 | 100 | 100 |

The reaction pressure was 3.5 MPa. Oligomerization achievements are shown in Table 10.

TABLE 10

| | Feed 2 | Feed 3 | Feed 4 |
|---|---|---|---|
| WHSV, hr$^{-1}$ | .75 | 1.5 | .75 |
| Pressure, MPa | 3.5 | 3.5 | 6.2 |
| Inlet Temperature, ° C. | 190 | 170 | 178 |
| Maximum Temperature, ° C. | 198 | 192 | 198 |
| $C_4$ olefin conversion, % | 95 | 92 | 93 |
| $nC_4$ olefin conversion, % | 95 | 90 | 93 |
| $C_5$ olefin conversion, % | 90 | n/a | 86 |
| $C_5$-$C_7$ selectivity, wt % | 8 | 5 | 8 |
| $C_8$-$C_{11}$ selectivity, wt % | 77 | 79 | 77 |
| $C_{12}$-$C_{15}$ selectivity, wt % | 15 | 16 | 15 |
| $C_{16}$+ selectivity, wt % | 0.3 | 0.1 | .01 |
| Total $C_9$+ selectivity, wt % | 35 | 20 | 25 |
| Total $C_{12}$+ selectivity, wt % | 17 | 16 | 15 |
| Net gasoline yield, wt % | 94 | 92 | 91 |
| Net distillate yield, wt % | 32 | 18 | 23 |
| RONC (±3) | 97 | 96 | 96 |
| Engler T-90, ° C. | 182 | 164 | 182 |

Olefin conversion was at least 90% and normal butene conversion was over 90%. Normal $C_4$ olefin conversion reached 90% with $C_5$ olefins in Feed 2 and was 97% without $C_5$ olefins in Feed 1. $C_5$ olefin conversion reached 90% but was less when both iso and normal $C_5$ olefins were in the feed.

It can be seen that the SPA catalyst minimized the formation of $C_{12}$+ species to below 20 wt % at 16 and 17 wt %, respectively, without and with $C_5$ olefins in the oligomerization feed stream. When normal $C_5$ olefins were added, $C_{12}$+ formation reduced to 15 wt %. The $C_6$+ oligomerate produced by all three feeds met the gasoline T-90 spec indicating that 90 wt % boiled at temperatures under 193° C. (380° F.). The Research Octane Number for all three products was high, over 95, with and without substantial $C_5$ olefins present.

Example 5

Feed 2 with $C_5$ olefins present was subjected to oligomerization with Catalyst B, SPA, at different conditions to obtain different butene conversions. $C_5$ olefin is made up of 2-methyl-2-butene and 3-methyl-1-buene which comprises 9.16 wt % of the reaction mixture representing about a third of the olefins in the feed. Propylene was present at less than 0.1 wt %. Table 11 shows the legend of component olefins illustrated in FIG. 5.

TABLE 11

Figure 5:
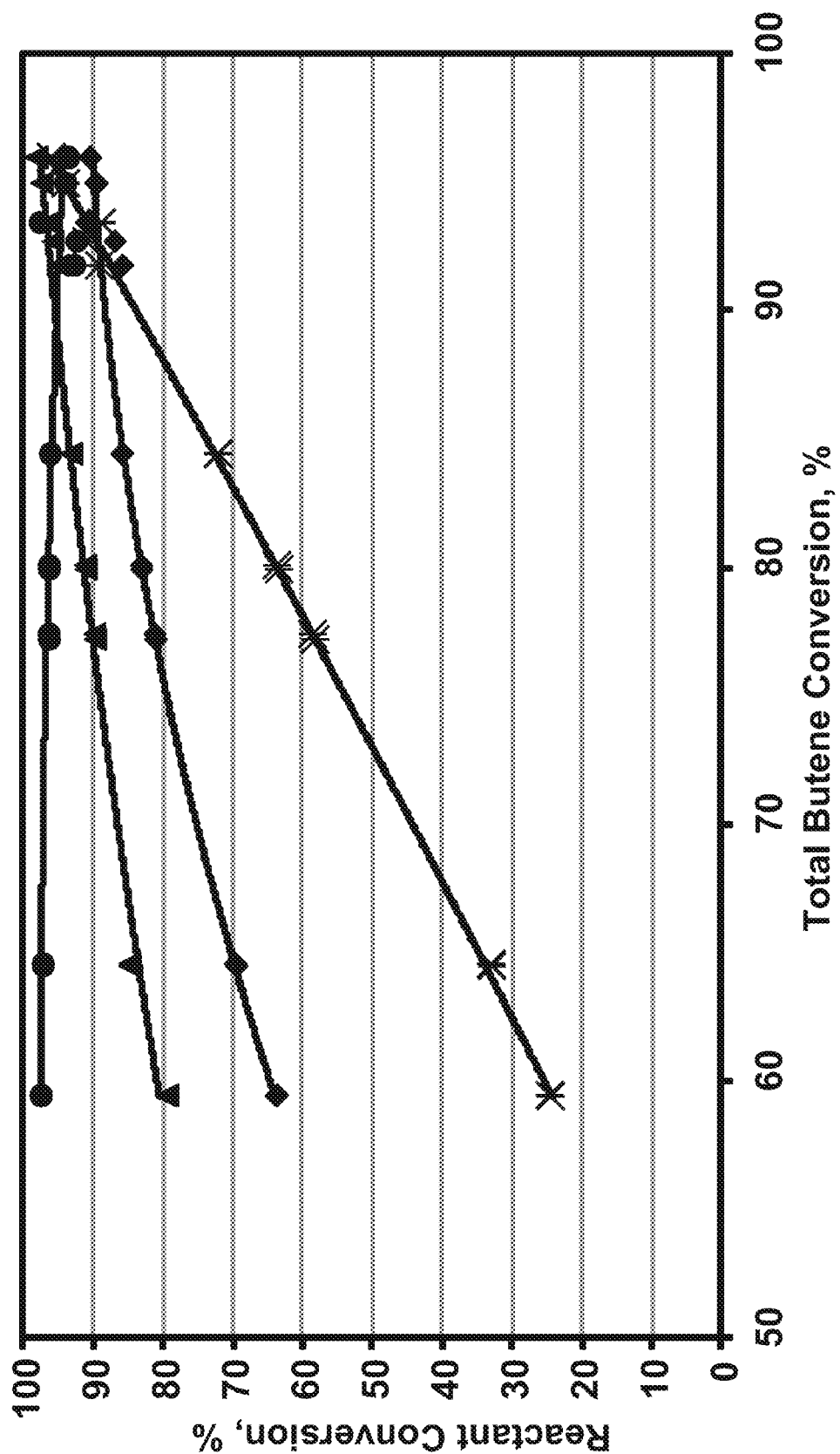
FIG. 5 is a plot of reactant conversion versus total butene conversion.

| Component | Symbols in FIG. 5 |
|---|---|
| isobutylene | Circle |
| 1-butene | Triangle |
| 2-methyl-2-butene and 3-met-1-butene | Diamond |
| 2-butene (cis & trans) | Asterisk |

FIG. 5 shows conversions for each of the olefins in Feed 2 over Catalyst B, SPA. Over 95% conversion of normal $C_4$ olefins was achieved at over 90% butene conversion. Pentene conversion reached 90% at over 90% butene conversion. Normal butene conversion actually exceeded isobutene conversion at high butene conversion over about 95%.

Example 6

Three feeds were oligomerized to demonstrate the ability of Catalyst A, MTT, to produce diesel range oligomerate by recycling gasoline range oligomerate to the oligomerization zone. Feed 1 from Example 1 with an isobutane diluent was tested along with Feed 5 which had a normal hexane diluent and Feed 6 which had an isobutane diluent but spiked with diisobutene to represent recycled gasoline range oligomers. The feeds are shown in Table 12. The symbols in FIG. 6 correspond to those indicated in the last row of Table 12.

TABLE 12

Figure 6:
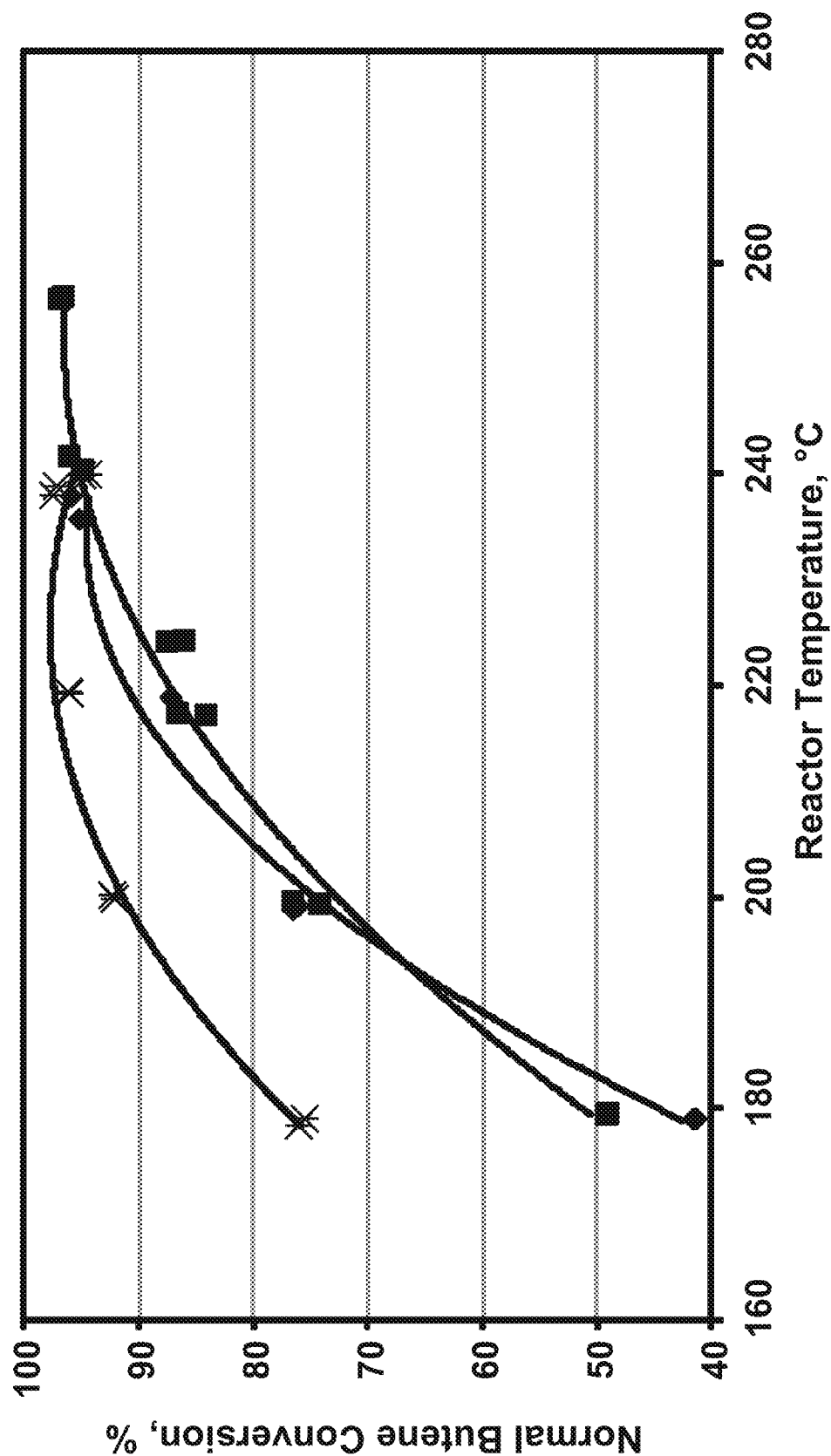
FIG. 6 is a plot of normal butene conversion versus reactor temperature.

| Component | Feed 1 Fraction, wt % | Feed 5 Fraction, wt % | Feed 6 Fraction, wt % |
|---|---|---|---|
| propylene | 0.1 | 0.08 | 0.08 |
| isobutane | 70.04 | 15.75 | 15.75 |
| isobutylene | 7.7 | 7.3 | 7.3 |
| 1-butene | 5.7 | 5.1 | 5.1 |
| 2-butene (cis & trans) | 16.28 | 11.6 | 11.6 |
| 3-met-1-butene | 0.16 | 0.16 | 0.16 |
| n-hexane | 0 | 60 | 0 |
| acetone | 0.02 | 0.01 | 0.01 |
| tert-butyl alcohol | 0 | 0.0008 | 0.0008 |
| diisobutene | 0 | 0 | 60 |
| Total | 100 | 100 | 100 |
| FIG. 6 symbol | square | diamond | asterisk |

The oligomerization conditions included 6.2 MPa pressure, 0.75 WHSV over Catalyst A, MTT. Normal butene conversion as a function of temperature is graphed in FIG. 6 for the three feeds.

Figure 7:
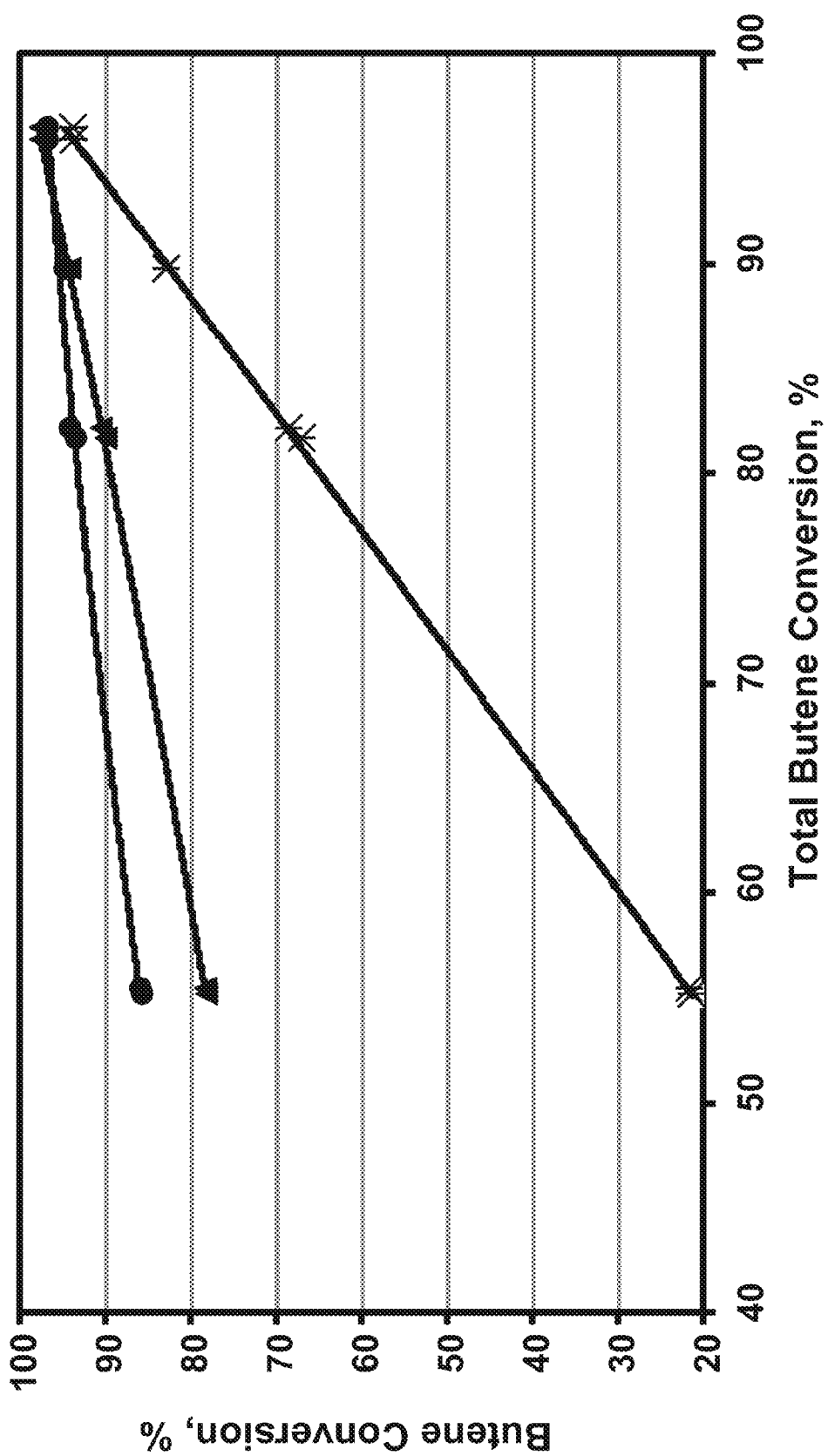
FIGS. 7 and 8 are plots of butene conversion versus total butene conversion.
Figure 8:
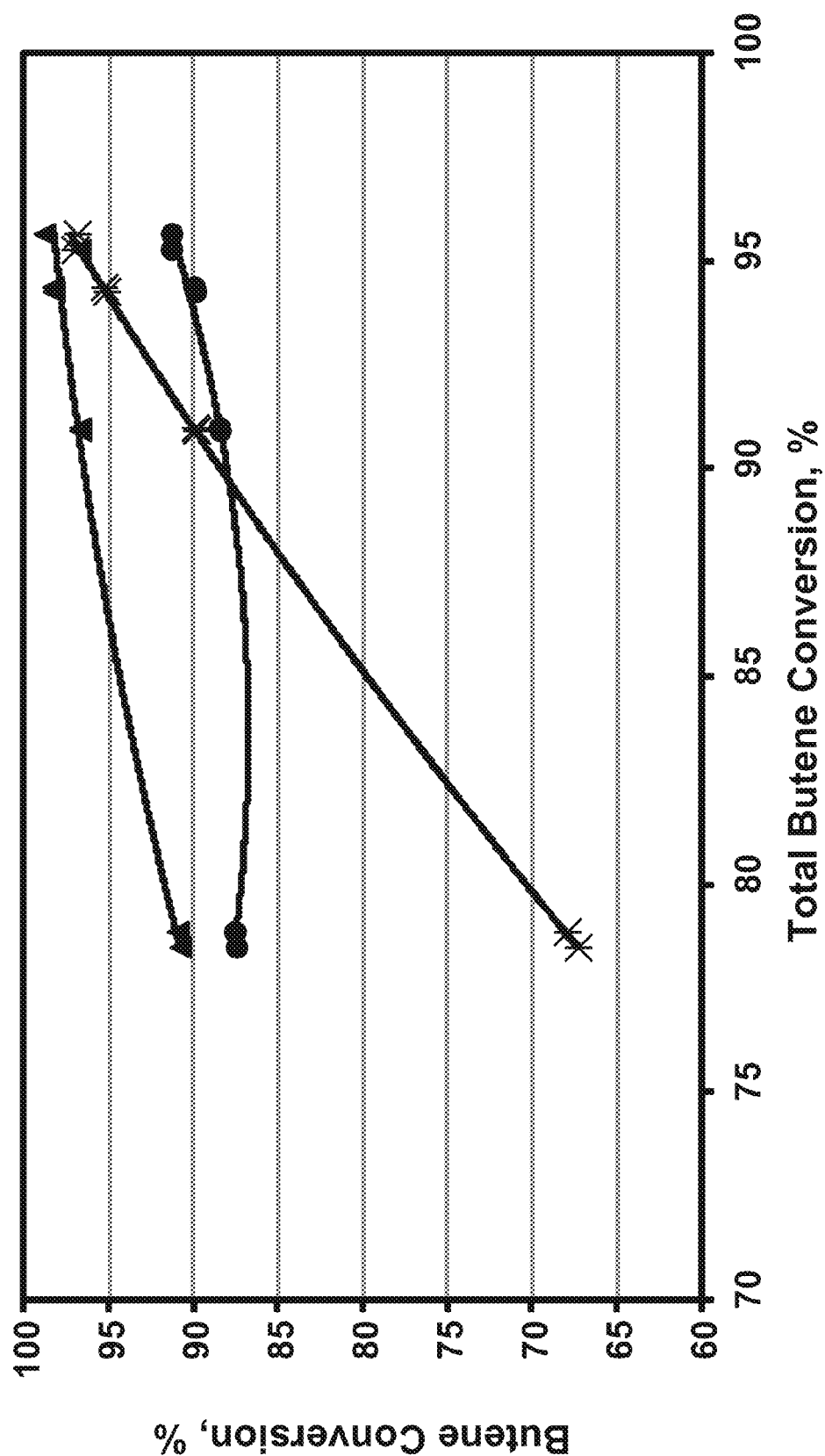

FIG. 6 demonstrates that Feed 6 with the diisobutene oligomer has greater normal butene conversion at equivalent temperatures between 180° and 240° C. Consequently, gasoline oligomerate recycle to the oligomerization zone will improve normal $C_4$ conversion. Butene conversion for Feed 5 is shown in FIG. 7 and for Feed 6 is shown in FIG. 8. The key for FIGS. 7 and 8 is shown in Table 13.

TABLE 13

| Component | Symbols in FIGS. 7 & 8 |
| --- | --- |
| isobutylene | Circle |
| 1-butene | Triangle |
| 2-butene (cis & trans) | Asterisk |

At higher butene conversions and with diisobutene recycle, isobutene has the lowest conversion with both 1-butene and 2-butene having greater oligomerization to oligomers. However, without diisobutene recycle, isobutene undergoes the greatest conversion, but with 1-butene conversion apparently surpassing isobutene conversion at over 94% total butene conversion. We expect the same performance for Feed 1 with isobutane diluent.

Table 14 gives feed performance for the three feeds at conditions selected to achieve high butene conversion and high $C_{12}+$ yield including 6.2 MPa of pressure.

TABLE 14

| Run | Feed 1 | Feed 5 | Feed 6 |
| --- | --- | --- | --- |
| WHSV, hr$^{-1}$ | 0.9 | 0.6 | 0.7 |
| Maximum Bed Temperature, ° C. | 240 | 236 | 239 |
| $C_4$ olefin conversion, % | 95 | 96 | 95 |
| n-$C_4$ olefin conversion, % | 95 | 95 | 97 |
| i-$C_4$ olefin conversion, % | 96 | 97 | 91 |
| 1-$C_4$ olefin conversion, % | 97 | 98 | 97 |
| 2-$C_4$ olefin conversion, % | 94 | 94 | 97 |
| $C_5$-$C_7$ selectivity, wt % | 3 | 3 | 0.8 |
| $C_8$-$C_{11}$ selectivity, wt % | 27 | 27 | 26 |
| $C_{12}$-$C_{15}$ selectivity, wt % | 49 | 52 | 39 |
| $C_{16}+$ selectivity, wt % | 20 | 19 | 34 |
| Total $C_9+$ selectivity, wt % | 76 | 77 | 77 |
| Total $C_{12}+$ selectivity, wt % | 70 | 71 | 73 |
| Diesel Yield, wt % | 72 | 74 | 73 |

$C_{12}+$ selectivity increased and $C_{16}+$ increased substantially with diisobutene presence over the feeds without diisobutene presence. Yield calculated by multiplying $C_4$ olefin conversion by total $C_9+$ selectivity taken at the 150° C. (300° F.) cut point was over 70% for all feeds based on a single pass through the oligomerization reactor.

Example 7

Figure 9:
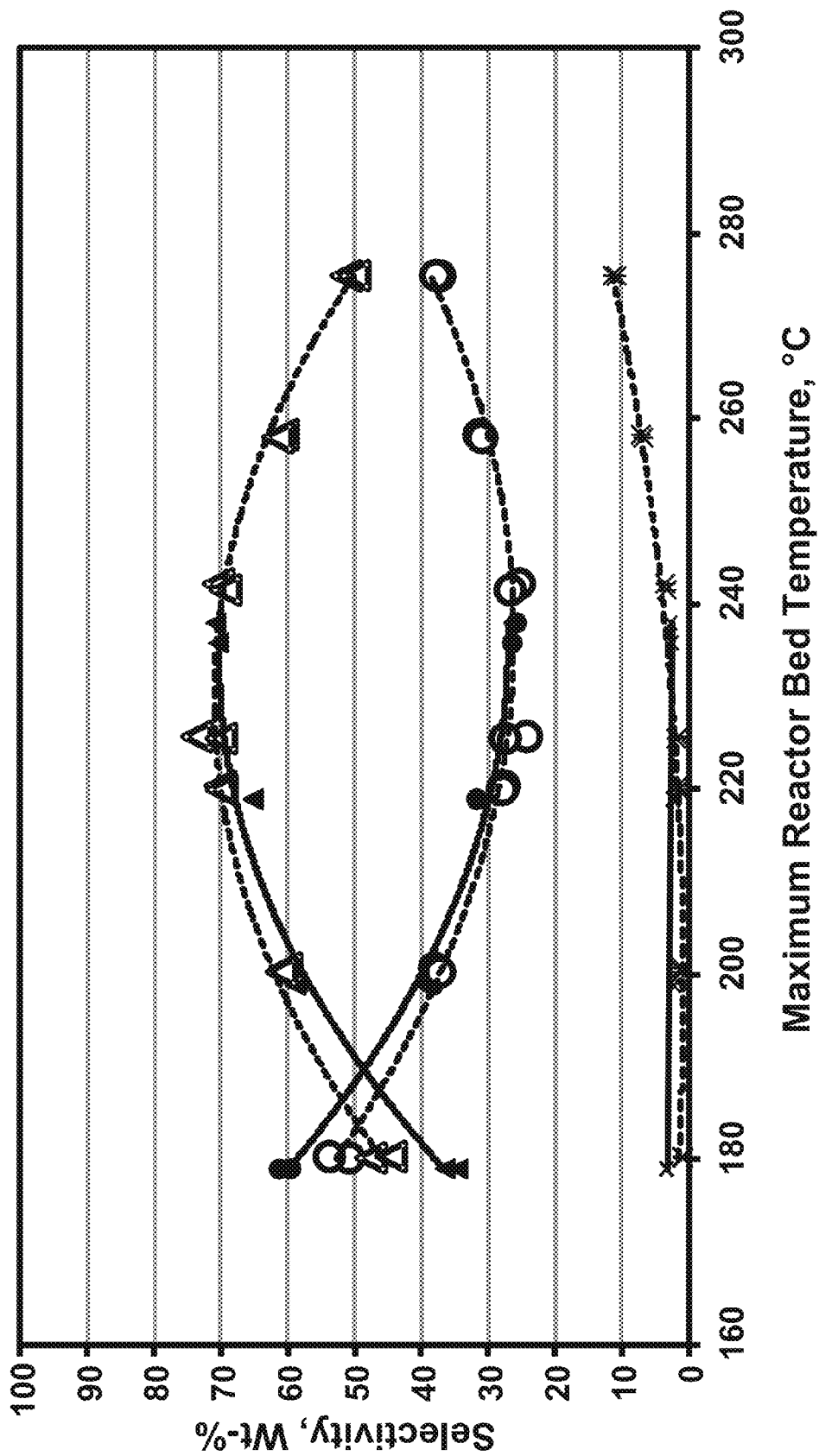
FIG. 9 is a plot of selectivity versus maximum reactor bed temperature.

Feed 1 and Feed 5 were reacted over Catalyst A, MTT, at 6.2 MPa and 0.75 WHSV. A graph of selectivity as a function of maximum catalyst bed temperature in FIG. 9 shows optimal maximum bed temperature between about 220° and about 240° C. has an apex that corresponds with maximal $C_{12}+$ olefin selectivity and to a minimum $C_8$-$C_{11}$ olefin selectivity and a $C_5$-$C_7$ olefin selectivity. Table 15 provides a key for FIG. 9. In FIG. 9, solid points and lines represent Feed 1; whereas; hollow points and dashed lines represent Feed 5.

TABLE 15

| Symbol | Solid - Feed 1 | Hollow - Feed 5 |
| --- | --- | --- |
| $C_{12}+$ olefin selectivity | Triangles | |
| $C_8$-$C_{11}$ olefin selectivity | Circles | |
| $C_5$-$C_7$ olefin selectivity | Greek Crosses | Asterisks |

Example 8

Three different feeds representing product oligomerate were subjected to micro reactor cracking testing over three different catalysts. The three feeds were 2,4,4-trimethyl-1-pentene, 1-octene and mixed $C_{12}$ and larger olefins which contained linear molecules. The three catalysts included a ZSM-5 additive with 40 wt % ZSM-5 crystals, Zeolite Y and a blend of 25 wt % of the ZSM-5 additive and 75 wt % Zeolite Y such that 10 wt % of the blend was ZSM-5 crystals. The test conditions included 565° C., 10.3 kPa (gauge) and a residence time of 0.05 seconds at standard feed conditions of 25° C. and atmospheric pressure. The feeds were a mixture of 10 mol-% hydrocarbon, 5 mol-% steam, and the balance nitrogen. Table 16 provides the key for FIGS. 10-12.

TABLE 16

Figure 10:
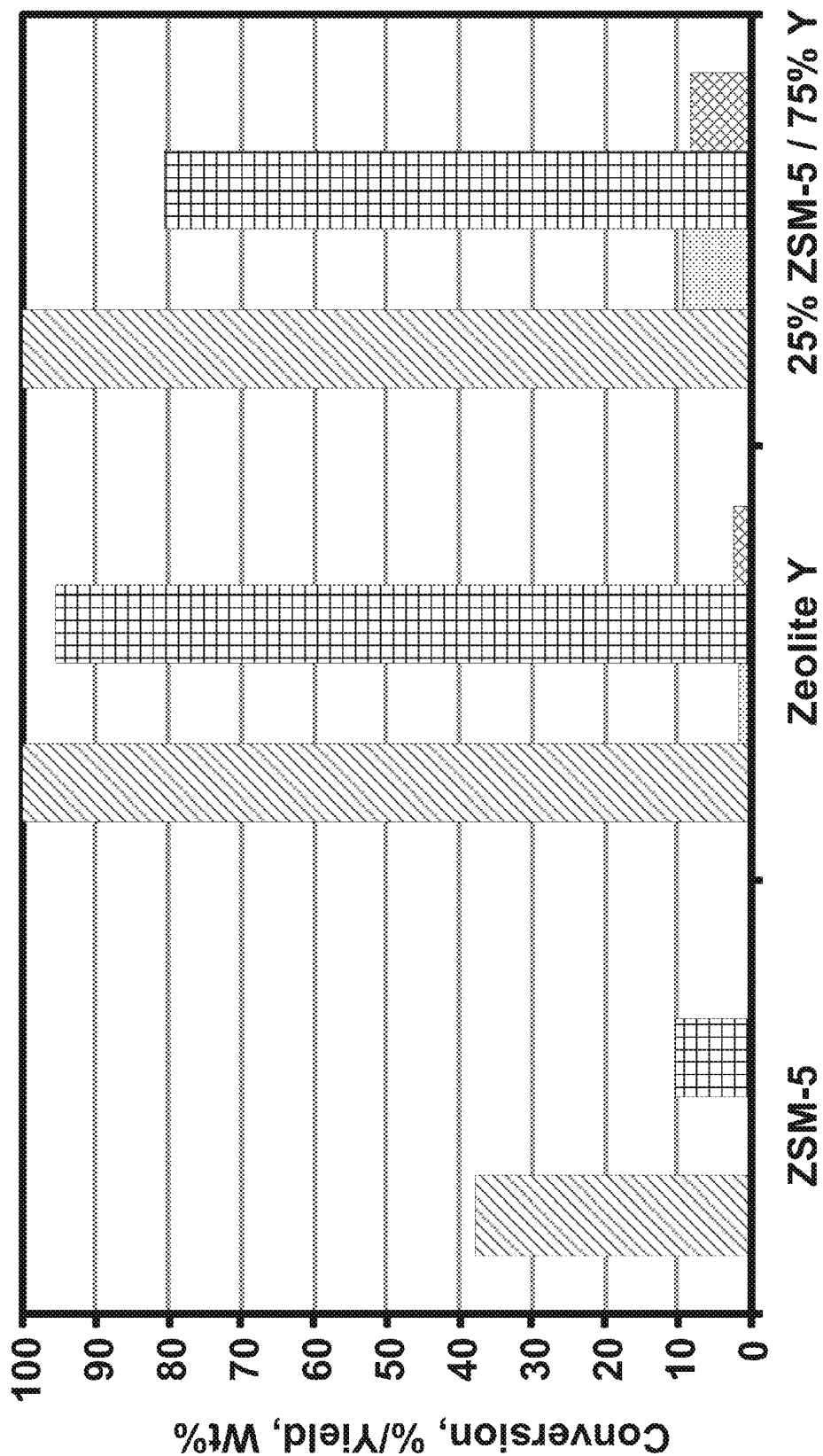
FIGS. 10-12 are bar graphs of conversion and yield for three different catalysts.
Figure 11:
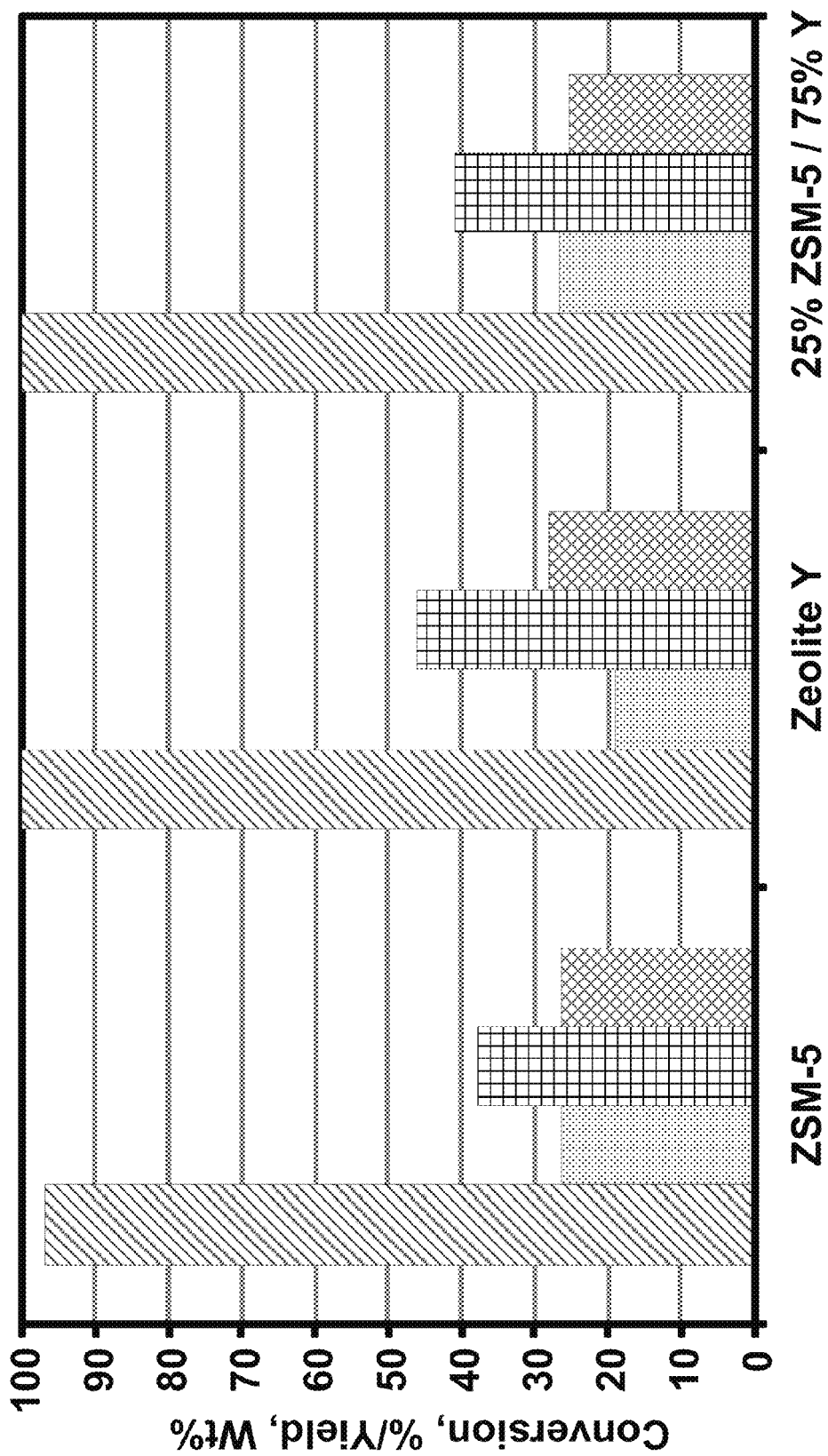
Figure 12:
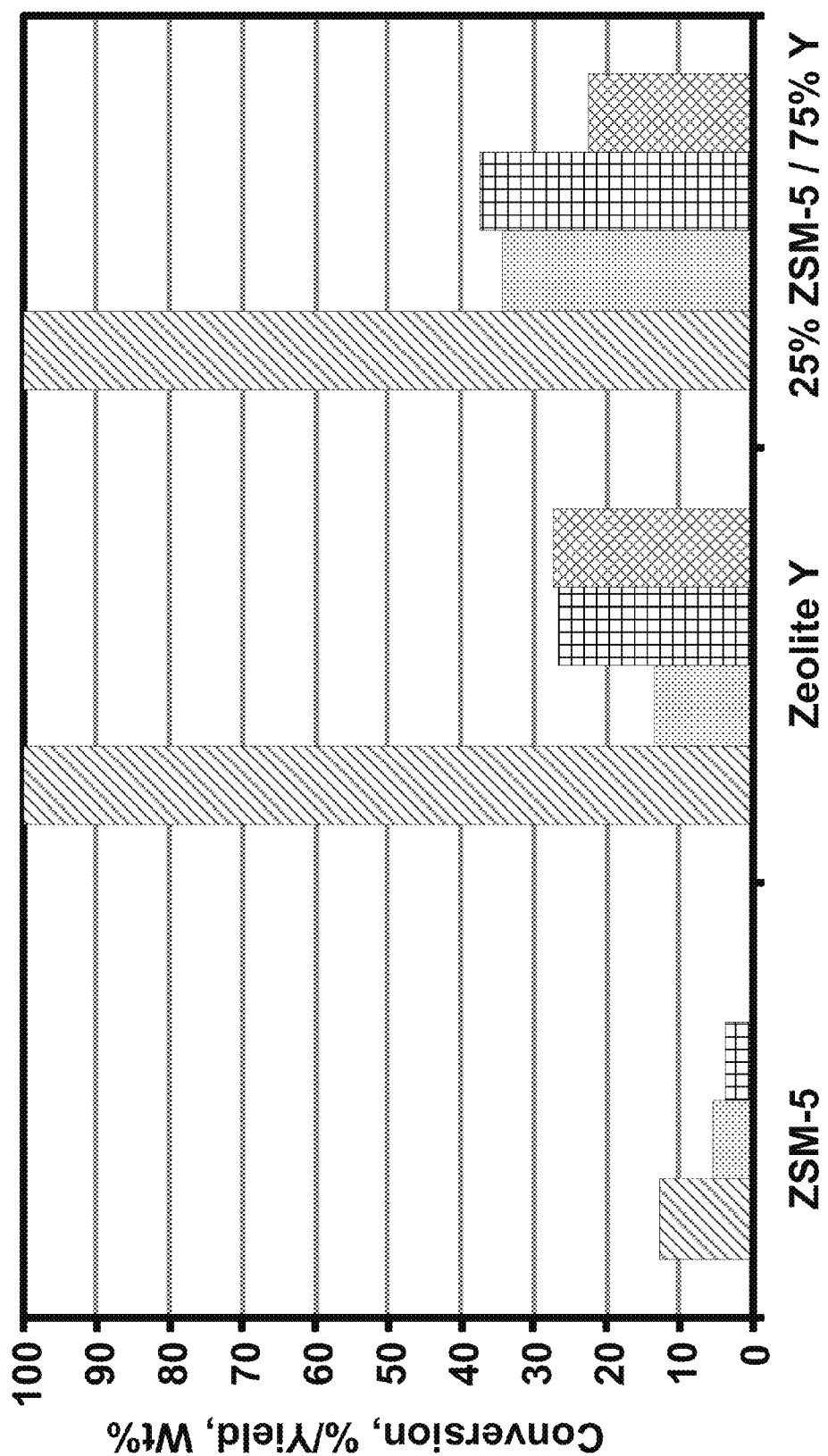

| Component | Key |
| --- | --- |
| Conversion, % | Diagonal lines |
| $C_3$ olefin yield, wt % | Dotted fill |
| $C_4$ olefin yield, wt % | Cross Hatch |
| $C_5$ olefin yield, wt % | Diagonal Cross Hatch |
| ZSM-5 | Left |
| Zeolite Y | Middle |
| Blend of ZSM-5 and Zeolite Y | Right |
| Trimethyl pentene feed | FIG. 10 |
| 1-Octene feed | FIG. 11 |
| Mixed $C_{12}$ olefins | FIG. 12 |

FIG. 10 reveals that achieving high conversion of 2,4,4,-trimethyl-1-pentene over ZSM-5 alone was very difficult. The same feed over Zeolite Y or the blend of ZSM-5 and Zeolite Y reached high conversion easily. The blend of ZSM-5 and Y zeolite had the highest propylene yield. FIG. 11 shows that the conversion of 1-octene was very high over all three catalysts. We saw a similar pattern for methyl heptene in a separate test. Again, the blend of ZSM-5 and Y zeolite had the highest propylene yield. FIG. 12 shows that conversion of $C_{12}$ and larger olefins, propylene tetramer, over the blend of ZSM-5 and Y zeolite had the highest propylene yield of all the feeds tested. ZSM-5 alone was not able to achieve much conversion of the $C_{12}$ and larger olefin feed.

This example establishes that feeding oligomerate produced over Catalyst A of Example 1, MTT, which produces less of the trimethyl pentene but more of the linear and less-branched $C_8$ olefins and $C_{12}$ olefins to an FCC unit will provide the best FCC feed to crack into the most propylene.

Example 9

Figure 13:
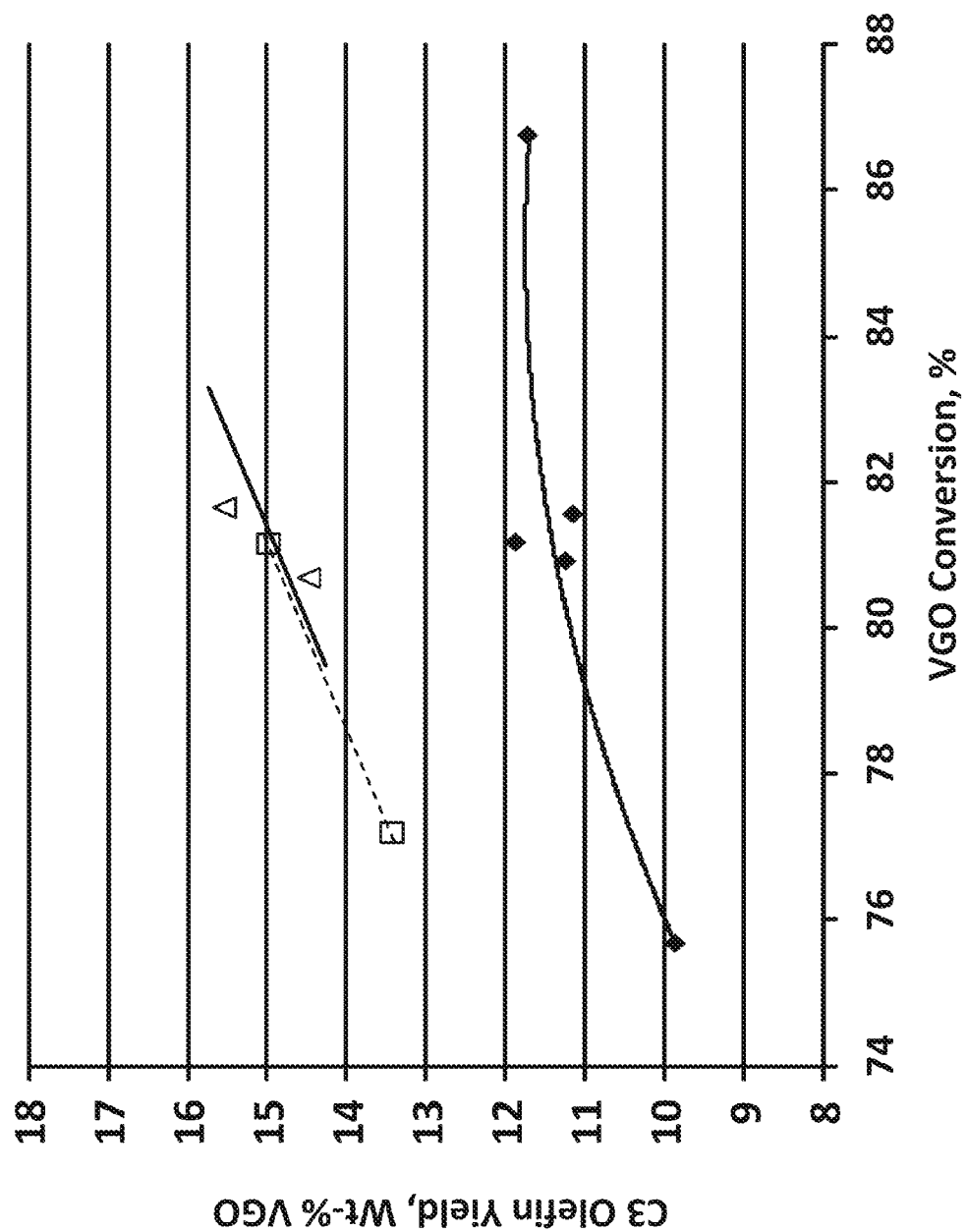
FIG. 13 is a plot of $C_3$ olefin yield versus VGO conversion.

Three feeds were reacted over FCC equilibrium catalyst comprising 8 wt % ZSM-5. Feed 7 comprised hydrotreated VGO with a hydrogen content of 13.0 wt %. Feed 8 comprised the same VGO mixed with 25 wt % oligomerate product catalyzed by Catalyst A of Example 1. Feed 9 comprised the same VGO mixed with 25 wt % oligomerate product catalyzed by Catalyst B of Example 1. The feeds were heated to 260-287° C. and contacted with the FCC catalyst in a riser apparatus to achieve 2.5-3.0 seconds of residence time. FIG. 13 plots $C_3$ olefin yield versus VGO conversion. The key for FIG. 13 is in Table 17.

TABLE 17

| Feed | Composition | Key |
|---|---|---|
| Feed 7 | VGO | Solid diamond |
| Feed 8 | VGO/MTT oligomerate | Square |
| Feed 9 | VGO/SPA oligomerate | Triangle |

FIG. 13 shows that recycle of oligomerate product to the FCC zone can boost propylene production. At the apex of the propylene yield curve of VGO alone, the feed comprising VGO and oligomerate provided 3.2 wt % more propylene yield from the FCC zone.

Specific Embodiments

While the following is described in conjunction with specific embodiments, it will be understood that this description is intended to illustrate and not limit the scope of the preceding description and the appended claims.

A first embodiment of the invention is a process for making distillate comprising feeding an oligomerization feed stream comprising $C_4$ olefins to an oligomerization zone; recycling a gasoline stream comprising $C_8$ olefins to the oligomerization zone; oligomerizing $C_4$ olefins with $C_4$ olefins and $C_8$ olefins in the oligomerization zone; separating an oligomerate stream from the oligomerization zone in a recovery zone to provide a distillate stream comprising distillate hydrocarbons and the gasoline recycle stream. An embodiment of the invention is one, any or all of prior embodiments in this paragraph up through the first embodiment in this paragraph further comprising oligomerizing a greater proportion of normal butenes than isobutenes. An embodiment of the invention is one, any or all of prior embodiments in this paragraph up through the first embodiment in this paragraph further comprising oligomerizing the $C_4$ olefins with others of the $C_4$ olefins and the $C_8$ olefins over a zeolite catalyst having a uni-dimensional 10-ring pore structure. An embodiment of the invention is one, any or all of prior embodiments in this paragraph up through the first embodiment in this paragraph wherein the zeolite catalyst is an MTT. An embodiment of the invention is one, any or all of prior embodiments in this paragraph up through the first embodiment in this paragraph wherein the maximum temperature of a bed of the zeolite catalyst is between about 200 and about 250° C. An embodiment of the invention is one, any or all of prior embodiments in this paragraph up through the first embodiment in this paragraph wherein the oligomerate stream comprises greater than 30 wt % $C_9$+ olefins. An embodiment of the invention is one, any or all of prior embodiments in this paragraph up through the first embodiment in this paragraph wherein oligomerization feed stream also comprises $C_5$ olefins and the $C_4$ olefins also oligomerize with the $C_5$ olefins and the $C_4$ olefins and $C_5$ olefins oligomerize with the $C_8$ olefins in the oligomerization zone. An embodiment of the invention is one, any or all of prior embodiments in this paragraph up through the first embodiment in this paragraph further comprising purging a purge intermediate stream comprising $C_5$ hydrocarbons from the recovery zone. An embodiment of the invention is one, any or all of prior embodiments in this paragraph up through the first embodiment in this paragraph further comprising operating an oligomerization reactor in the oligomerization zone to allow the temperature at the outlet to be over about 25° C. greater than the temperature at the inlet. An embodiment of the invention is one, any or all of prior embodiments in this paragraph up through the first embodiment in this paragraph further comprising separating the gasoline recycle stream from the distillate stream in a distillate separator column.

A second embodiment of the invention is a process for making distillate comprising feeding an oligomerization feed stream comprising $C_4$ and $C_5$ olefins to an oligomerization zone; recycling a gasoline recycle stream comprising C8 olefins to the oligomerization zone; oligomerizing $C_4$ olefins with $C_4$ olefins, $C_5$ olefins and $C_8$ olefins and $C_5$ olefins with $C_8$ olefins in the oligomerization zone; and separating an oligomerate stream from the oligomerization zone in a recovery zone to provide a distillate stream comprising distillate hydrocarbons and the gasoline recycle stream. An embodiment of the invention is one, any or all of prior embodiments in this paragraph up through the second embodiment in this paragraph further comprising oligomerizing the $C_4$ olefins, the $C_5$ olefins and the C8 olefins over an MTT zeolite catalyst. An embodiment of the invention is one, any or all of prior embodiments in this paragraph up through the second embodiment in this paragraph further comprising oligomerizing a greater proportion of normal butenes than isobutenes. An embodiment of the invention is one, any or all of prior embodiments in this paragraph up through the second embodiment in this paragraph further comprising operating an oligomerization reactor in the oligomerization zone to allow the temperature at the outlet to be over about 25° C. greater than the temperature at the inlet. An embodiment of the invention is one, any or all of prior embodiments in this paragraph up through the second embodiment in this paragraph wherein the maximum temperature of a bed of the zeolite catalyst is between about 200 and about 250° C. An embodiment of the invention is one, any or all of prior embodiments in this paragraph up through the second embodiment in this paragraph wherein the oligomerate stream comprises greater than 30 wt % $C_9$+ olefins.

A third embodiment of the invention is a process for making distillate comprising feeding an oligomerization feed stream comprising $C_4$ olefins to an oligomerization zone; recycling a gasoline recycle stream comprising $C_8$ olefins to the oligomerization zone; oligomerizing $C_4$ olefins with $C_4$ olefins and $C_8$ olefins in the oligomerization zone over an MTT zeolite catalyst; and separating an oligomerate stream from the oligomerization zone in a recovery zone to provide a distillate stream comprising distillate hydrocarbons and the gasoline recycle stream. An embodiment of the invention is one, any or all of prior embodiments in this paragraph up through the third embodiment in this paragraph further comprising oligomerizing a greater proportion of normal butenes than isobutenes. An embodiment of the invention is one, any or all of prior embodiments in this paragraph up through the third embodiment in this paragraph wherein the maximum temperature of a bed of the zeolite catalyst is between about 200 and about 250° C. An embodiment of the invention is one, any or all of prior embodiments in this paragraph up through the third embodiment in this paragraph further comprising operating an oligomerization reactor in the oligomerization zone to allow the temperature at the outlet to be over about 25° C. greater than the temperature at the inlet.

Without further elaboration, it is believed that one skilled in the art can, using the preceding description, utilize the present invention to its fullest extent. Preferred embodiments of this invention are described herein, including the best mode known to the inventors for carrying out the invention. The preceding preferred specific embodiments are, therefore, to be construed as merely illustrative, and not limitative of the remainder of the disclosure in any way whatsoever.

In the foregoing, all temperatures are set forth in degrees Celsius and, all parts and percentages are by weight, unless otherwise indicated. Pressures are given at the vessel outlet and particularly at the vapor outlet in vessels with multiple outlets. Control valves should be opened or closed as consistent with the intent of the disclosure.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for making distillate comprising:
   feeding an oligomerization feed stream comprising $C_4$ olefins to an oligomerization zone;
   recycling a gasoline recycle stream comprising $C_8$ olefins to said oligomerization zone;
   oligomerizing $C_4$ olefins with $C_4$ olefins and $C_8$ olefins in said oligomerization zone over an MTT zeolite catalyst, wherein a greater proportion of normal butenes are oligomerized than isobutenes;
   separating an oligomerate stream from said oligomerization zone in a recovery zone to provide a distillate stream comprising distillate hydrocarbons and said gasoline recycle stream.

2. The process of claim 1 further comprising oligomerizing said $C_4$ olefins with others of said $C_4$ olefins and said $C_8$ olefins over a zeolite catalyst having a uni-dimensional 10-ring pore structure.

3. The process of claim 1 wherein said oligomerate stream comprises greater than 30 wt % $C_9$+ olefins.

4. The process of claim 1 wherein oligomerization feed stream also comprises $C_5$ olefins and said $C_4$ olefins also oligomerize with said $C_5$ olefins and said $C_4$ olefins and $C_5$ olefins oligomerize with said $C_8$ olefins in said oligomerization zone.

5. The process of claim 1 further comprising purging a purge intermediate stream comprising $C_5$ hydrocarbons from said recovery zone.

6. The process of claim 1 further comprising operating an oligomerization reactor in the oligomerization zone to allow the temperature at the outlet to be over about 25° C. greater than the temperature at the inlet.

7. The process of claim 1 further comprising separating said gasoline recycle stream from said distillate stream in a distillate separator column.

8. A process for making distillate comprising:
   feeding an oligomerization feed stream comprising $C_4$ olefins to an oligomerization zone;
   recycling a gasoline recycle stream comprising $C_8$ olefins to said oligomerization zone;
   oligomerizing $C_4$ olefins with C4 olefins and $C_8$ olefins in said oligomerization zone over over a bed of MTT zeolite catalyst having a temperature of between about 200 and about 250° C., wherein a greater proportion of normal butenes are oligomerized than isobutenes; and
   separating an oligomerate stream from said oligomerization zone in a recovery zone to provide a distillate stream comprising distillate hydrocarbons and said gasoline recycle stream.

9. The process of claim 8 further comprising operating an oligomerization reactor in the oligomerization zone to allow the temperature at the outlet to be over about 25° C. greater than the temperature at the inlet.

* * * * *